(12) United States Patent
Bae et al.

(10) Patent No.: US 12,233,282 B2
(45) Date of Patent: Feb. 25, 2025

(54) LIGHT RADIATION DEVICE FOR MEDICAL TREATMENT

(71) Applicant: SEOUL VIOSYS CO., LTD., Ansan-si (KR)

(72) Inventors: Hee Ho Bae, Ansan-si (KR); Yeong Min Yoon, Ansan-si (KR); A Young Lee, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 0 days.

(21) Appl. No.: 17/965,087

(22) Filed: Oct. 13, 2022

(65) Prior Publication Data

US 2023/0045570 A1   Feb. 9, 2023

Related U.S. Application Data

(63) Continuation of application No. 16/747,688, filed on Jan. 21, 2020, now abandoned.
(Continued)

(51) Int. Cl.
*A61N 5/06* (2006.01)
*A61L 2/08* (2006.01)
*A61L 2/10* (2006.01)

(52) U.S. Cl.
CPC ............ *A61N 5/0624* (2013.01); *A61L 2/084* (2013.01); *A61L 2/10* (2013.01); *A61N 2005/0661* (2013.01); *A61N 2005/0662* (2013.01)

(58) Field of Classification Search
CPC .......... A61N 5/0624; A61N 2005/0661; A61N 2005/0662; A61N 5/0616;
(Continued)

(56) References Cited

U.S. PATENT DOCUMENTS 6,290,713 B1   9/2001 Russell
2003/0153962 A1   8/2003 Cumbie
(Continued)

FOREIGN PATENT DOCUMENTS

JP   2008528188 A   7/2008
JP   2012514498 A   6/2012
(Continued)

OTHER PUBLICATIONS

European Search Report from corresponding European Patent Application No. 20744759.0, dated Nov. 7, 2022 (6 pages).
(Continued)

*Primary Examiner* — Joseph M Dietrich
*Assistant Examiner* — Michael T. Holtzclaw
(74) *Attorney, Agent, or Firm* — Perkins Coie LLP

(57) ABSTRACT

A light radiation device includes a housing, a substrate provided in the housing, and a light source mounted on the substrate. The light source includes a first light source including at least one first light source to emit first light having a blue wavelength band, a second light source including at least one second light source to emit second light having an ultraviolet wavelength band, and a control unit to control the first light source and the second light source such that the second light source sequentially emits the second light after the first light source emits the first light. A dose of the second light source is less than $\vec{1}/10$ of a dose of the first light source.

20 Claims, 18 Drawing Sheets

Related U.S. Application Data

(60) Provisional application No. 62/825,993, filed on Mar. 29, 2019, provisional application No. 62/795,730, filed on Jan. 23, 2019.

(58) Field of Classification Search
CPC .... A61N 2005/0626; A61N 2005/0663; A61L 2/084; A61L 2/10; A61L 2202/21; A61L 2/0047
USPC .......................................................... 607/1, 88
See application file for complete search history.

(56) References Cited

U.S. PATENT DOCUMENTS

| | | |
|---|---|---|
| 2006/0167531 A1 | 7/2006 | Gertner et al. |
| 2006/0195165 A1 | 8/2006 | Gertner |
| 2007/0208395 A1 | 9/2007 | Leclerc et al. |
| 2008/0071330 A1 | 3/2008 | Quisenberry et al. |
| 2008/0103560 A1 | 5/2008 | Powell et al. |
| 2010/0179469 A1 | 7/2010 | Hammond et al. |
| 2016/0015962 A1 | 1/2016 | Shokoueinejad Maragheh et al. |
| 2018/0015298 A1 | 1/2018 | Iguchi et al. |
| 2018/0093107 A1 | 4/2018 | Ball |
| 2018/0178034 A1 | 6/2018 | Iguchi et al. |
| 2018/0318599 A1 | 11/2018 | Van Bommel et al. |
| 2019/0099613 A1 | 4/2019 | Estes et al. |
| 2020/0230435 A1 | 7/2020 | Bae et al. |

FOREIGN PATENT DOCUMENTS

| | | |
|---|---|---|
| KR | 101515992 | 5/2015 |
| KR | 10-2018-0038200 A | 4/2018 |
| KR | 1020180067499 | 6/2018 |
| WO | 2006081312 A2 | 8/2006 |
| WO | 2009004412 A1 | 1/2009 |

OTHER PUBLICATIONS

International Search Report for International Application PCT/KR2020/001167, mailed May 4, 2020.

English translation of Office Action from corresponding Chinese Patent Application No. 202080004267.1, dated Sep. 25, 2023 (16 pages).

Japanese Office Action from corresponding Japanese Patent Application No. 2021-543131, dated Oct. 17, 2023 (8 pages).

Office Action from corresponding Korean Patent Application No. 10-2021-7025132, issued on Nov. 1, 2024, (5 pages).

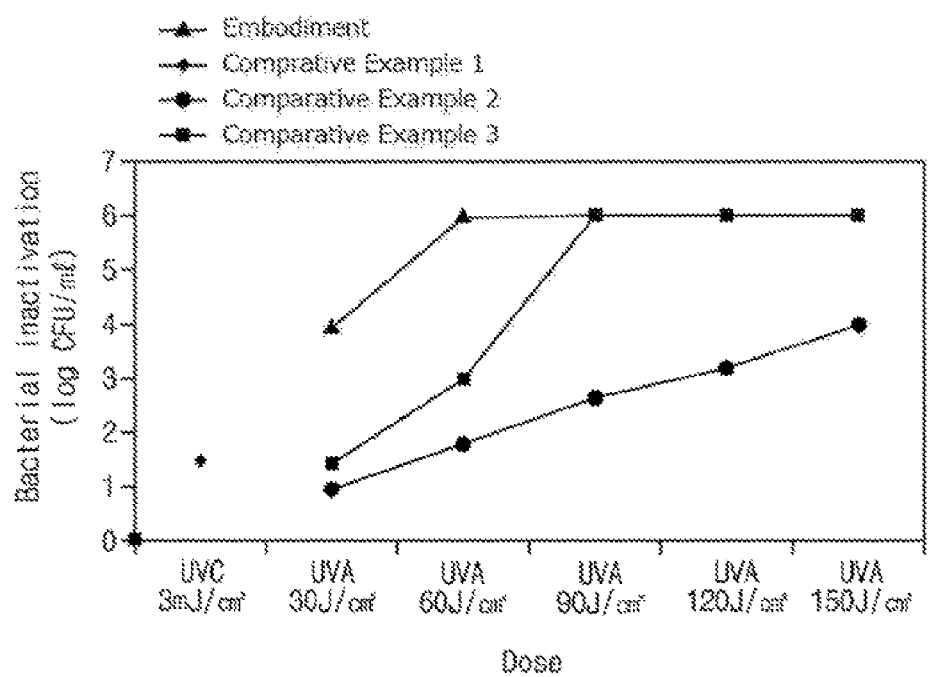

LIGHT RADIATION DEVICE FOR MEDICAL TREATMENT

PRIORITY AND CROSS-REFERENCE TO RELATED APPLICATIONS

This application is a continuation of U.S. patent application Ser. No. 16/747,688, filed on Jan. 21, 2020, which claims priority to U.S. Patent Application No. 62/795,730, filed on Jan. 23, 2019, and U.S. Patent Application No. 62/825,993, filed on Mar. 29, 2019. All the aforementioned applications are hereby incorporated by reference in their entireties.

RELATED ART

Embodiments of the present disclosure described herein relate to a light radiation device, and more particularly, relate to a light radiation device used for medical treatment.

Recently, various treatment devices using ultraviolet (UV) light have been developed. In general, it is well known that the UV light has a sterilization effect. A conventional UV treatment device employs a traditional UV lamp, operates the UV lamp near a skin, and irradiates the UV light to a part of the skin to be treated.

However, the UV light causes an adverse effect such as skin aging or cancer, in addition to the sterilization effect. Accordingly, there is a need to provide a process for obtaining the sterilization effect safely without any influence exerted on a human body.

SUMMARY

Embodiments of the present disclosure provide a light radiation device capable of obtaining a higher sterilization effect while minimizing an adverse effect on a human body.

According to an exemplary embodiment, a light radiation device includes a housing, a substrate provided in the housing, and a light source mounted on the substrate. The light source includes a first light source including at least one first light source and configured to emit first light having a blue wavelength band, a second light source including at least one second light source and configured to emit second light having a ultraviolet wavelength band, and a control unit to control light emission of the first light source and the second light source such that the first light and the second light are emitted, sequentially, or at times close to each other, even if the first light is superposed with the second light or is not superposed with the second light. A dose of the second light source is less than $\frac{1}{10}$ of a dose of the first light source.

According to an exemplary embodiment, the control unit may control the first light source and the second light source to emit the second light after starting to emit the first light.

According to an exemplary embodiment, the second light may correspond to at least one of UVA (ultraviolet A), UVB (ultraviolet B), and UVC (Ultraviolet C) wavelength bands.

According to an exemplary embodiment, the first light may have a wavelength band in a range of about 400 nm to about 500 nm. The first light may further include light having a wavelength band corresponding to a visible light, and the first light may have a wavelength band in a range of about 380 nm to about 780 nm. According to an exemplary embodiment, the second light may have a wavelength band in a range of about 240 nm to about 280 nm.

According to an exemplary embodiment, the first light may be irradiated for a first time, and the second light may be irradiated for a second time shorter than the first time.

According to an exemplary embodiment, the second light may be started to be irradiated after the first light is completely irradiated, the second light may be started to be irradiated before the first light is completely irradiated, and at least a portion of the first time and the second time may have a mutually overlapping duration. In addition, the first light may be continuously irradiated, and the second light may be discontinuously irradiated. According to an embodiment of the present invention, the second light may be periodically irradiated.

According to an exemplary embodiment, the light radiation device may be used to treat a human body. For example, the light radiation device may be used to treat acute wound.

According to an exemplary embodiment, on the assumption that a dose, which is in a harmless range, per day is an allowable dose when the second light is applied to a human body, the second light source may emit the second light within the allowable dose. According to an exemplary embodiment, the second light may be irradiated with a dose in a range of about 30 J/m2 to about 1,000,000 J/m2.

As described above, according to embodiments of the present disclosure, there is provided a light radiation device capable of obtaining a higher sterilization effect while minimizing adverse effect on a human body.

BRIEF DESCRIPTION OF THE DRAWINGS

The above and other objects and features of the present disclosure will become apparent by describing in detail exemplary embodiments thereof with reference to the accompanying drawings.

FIG. 3A, FIG. 3B and FIG. 3C illustrate different timings of turning on/off the first and second light sources, respectively;

FIG. 4A illustrates irradiating the first light followed by the sequential irradiation of the second light and FIG. 4B illustrates irradiating the second light followed by the sequential irradiation of the first light;

FIG. 5A illustrates one example of repeat patterns of a first light and a second light sources; FIG. 5B illustrates another example of repeat patterns of a first light and a second light; and FIG. 5C illustrates further another example of repeat patterns of a first light and a second light.

FIG. 10 is a graph illustrating and comparing a sterilization effect depending on irradiation conditions when a light is irradiated to a sterilization subject using a conventional light emitting device and a light emitting device according to an embodiment of the present disclosure;

FIGS. 19A and 19B are photographs obtained by capturing images of the shape of the wound area based on days, in which FIG. 19A is a photograph of wounds in a non-irradiation group, and FIG. 19B is a photograph of wounds in the light irradiation group;

DETAILED DESCRIPTION OF EMBODIMENTS

Figure 1:
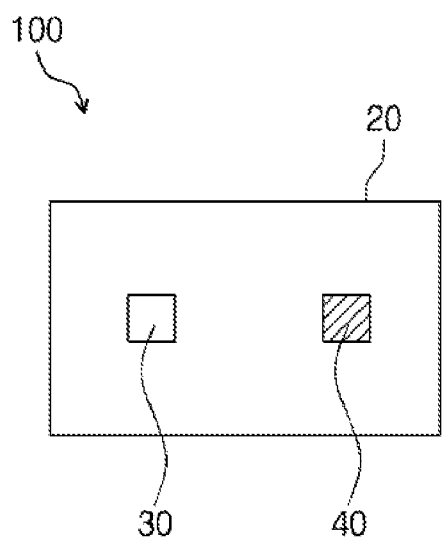
FIG. 1 is a plan view illustrating a light radiation device, according to an embodiment of the present disclosure.

While the invention is susceptible to various modifications and alternative forms, specific embodiments thereof are shown by way of example in the drawings and will be described herein in detail. It should be understood, however, that there is no intent to limit the invention to the particular forms disclosed, but on the contrary, the invention is to cover all modifications, equivalents, and alternatives falling within the spirit and scope of the invention.

Hereinafter, exemplary embodiments of the present disclosure will be described in more detail with reference to accompanying drawings.

The present disclosure relates to a light radiation device capable of sterilizing a target by applying a sterilizing light to the target. In particular, according to an embodiment of the present disclosure, the light radiation device may be used to treat a wound. When a target to be sterilized is a human body and the skin of the human body is wounded, it is necessary to sterilize a pathogen at the wounded part. A sterilizing device according to one embodiment of the present disclosure may be used to sterilize the pathogen in the wound. In this case, the pathogens refer to microorganisms such as bacteria, viruses, germs, fungi, protists, or moulds. According to embodiments of the present disclosure, the light radiation device may be used for various wounds such as a wound, an ulcer, surgical site infection, a laceration, an incised wound, or a punctured wound.

FIG. 1 is a plan view illustrating a light radiation device, according to an embodiment of the present disclosure.

According to embodiments of the present disclosure, a light radiation device 100 includes a first light source 30 to emit first light, a second light source 40 to emit second light, and a substrate 20 to mount the first and second light sources 30 and 40 thereon.

Since the first light source 30 and the second light source 40 are mounted on the substrate 20, the substrate 20 is not limited to a specific form and may be provided in various forms sufficient to mount the first and second light sources 30 and 40 thereon. The substrate 20 may be provided in the form of including a wiring to supply power to the first and second light sources 30 and 40. In some embodiments, the substrate 20 may include, for example, a metallic substrate or a printed circuit board including the wiring.

The first light source 30 may emit first light in a blue wavelength band of a visible light wavelength band. The first light may correspond to light in a wavelength band of about 400 nm to about 500 nm. In some embodiments of the present disclosure, the first light may have a wavelength band of about 400 nm to about 420 nm. More specifically, the first light may have a wavelength of 405 nm.

The first light acts on a photosensitizer present in microorganisms such as bacteria, germs, and moulds to damage the cell, thereby result in the death of the microorganisms. The first light corresponds to the absorption wavelength of porphyrin, which is a photosensitizer present in bacteria. The first light exhibits higher sterilization power, particularly, in the wavelength range of 400 nm to 420 nm. Additionally, the first light may be in the wavelength range of 455 nm to 470 nm, which corresponds to the absorption wavelength band of the porphyrin. The porphyrin is a pigment that is essential for the process of intracellular oxygen transfer. The porphyrin exhibits a higher absorption, particularly, in the wavelength range of about 402 nm to about 420 nm, and more particularly absorbs a wavelength in the range of about 455 nm to 470 nm. In an embodiment of the present disclosure, since the content of the porphyrin varies depending on the type of bacteria, the porphyrin may be used for destroying specific bacteria by adjusting the wavelength and the intensity of the first light. When the first light is applied to bacteria, the porphyrin in the bacteria absorbs the first light, and reactive oxygen species are produced in the cell of the bacteria due to the energy of the first light. The reactive oxygen species are accumulated in cells of the bacteria to oxidize cell walls of the bacteria, thereby destroying the bacteria.

The second light source 40 emits the second light in the UV wavelength band. In other words, the second light may be light having a wavelength band in the range of about 100 nm to about 400 nm, and may be UVA, UVB, or UVC. The UVA may have a wavelength band in the range of about 315 nm to about 400 nm, the UVB may have a wavelength band in the range of about 280 nm to about 315 nm, and the UVC may have a wavelength band in the range of about 100 nm to about 280 nm. In some embodiments of the present disclosure, the second light may correspond to the UVC, and may have a wavelength band in the range of about 240 nm to about 280 nm. More specifically, the second light may have the wavelength of 275 nm.

When the second light is applied to bacteria, the DNA in the bacteria absorbs the second light, and the DNA structure may be changed due to the energy of the second light. The absorption of light by the DNA causes the binding of thymine and adenine in the DNA to be broken. This is because a base such as purine or pyrimidine, which constitutes the DNA, strongly absorbs UV light. As a result of light absorption, a thymine dimer is formed. This process leads to the DNA mutation, and the mutated DNA causes the death of the bacteria since the mutated DNA has no ability of cell proliferation. The DNA may absorb light having a wavelength band in the range of about 240 nm to about 280 nm.

Figure 2:
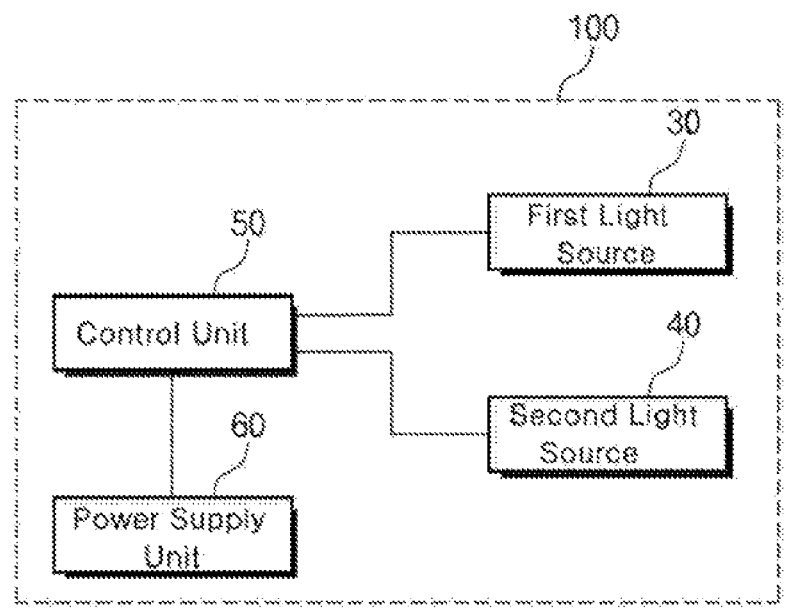
FIG. 2 is a block diagram illustrating a light radiation device, according to an embodiment of the present disclosure.

FIG. 2 is a block diagram illustrating the light radiation device, according to an embodiment of the present disclosure.

Referring to FIG. 2, according to embodiments of the present disclosure, the light radiation device 100 may include the first light source 30 to emit first light, the second light source 40 to emit second light, a control unit 50 to control the first light source 30 and the second light source 40, and a power supply unit 60 to supply power to the control unit 50 and the first and second light sources 30 and 40.

Each of the first and second light sources 30 and 40 may emit the first light including a blue wavelength band and the second light including a UV wavelength band, as described above. The first and second light sources 30 and 40 may be implemented with various types of light sources. For example, each of the first and second light sources 30 and 40 may independently use various types of light sources such as a light emitting diode, a halogen lamp, a fluorescent lamp, a gas discharge lamp, or a laser, and the types of the light sources are not limited.

The control unit 50 may control whether light is emitted from the first and second light sources 30 and 40, an amount of the light, the intensity of the light, or a time in which the light is emitted, such as a timing, a duration, etc. Additionally, or alternatively, the control unit 50 may control whether the light is emitted, an amount of the light, the intensity of the light, or the time in which the light is emitted, through various manners.

The power supply unit 60 is electrically connected with the first and second light sources 30 and 40 and the control unit 50 to supply power to the first and second light sources 30 and 40 and the control unit 50. Although the drawings illustrate that the power supply unit 60 supplies power to the first and second light sources 30 and 40 via the control unit 50, the present disclosure is not limited thereto. In other embodiments, the power supply unit 60 may be directly connected with the first and second light sources 30 and 40 to supply power.

The light radiation device 100 may further include an optical unit (not shown) to selectively collect or radiate light emitted from the first and second light sources 30 and 40. The optical unit may focus the light generated from the first and second light sources 30 and 40 to a small area, or a large area as necessary. Alternatively, the light may be focused or dispersed in a uniform or non-uniform depending on a position where the light is irradiated. The optical unit may include at least one lens, and the lens may perform various functions of focusing, dispersing, homogenizing, or non-homogenizing light from the first and second light sources 30 and 40.

For example, when a light is irradiated in the small area using the light emitting device 100, a lens for focusing the light from the first and second light sources 30 and 40 may be used. On the contrary, when a light is provided in the large area, for example, an entire room using the light emitting device 100 according to an exemplary embodiment, a lens for dispersing the light may be used.

In the present embodiment, the control unit 50 simultaneously, or individually drives the first light source 30 and the second light source 40. In other words, the first and second light sources 30 and 40 may be turned on/off simultaneously, or individually. In addition, even the intensities of light, that is, the first light and the second light emitted from the first and second light sources 30 and 40 may be simultaneously, or individually controlled.

In an embodiment of the present disclosure, the control unit 50 may allow a daily irradiation amount to be 3 mJ/cm$^2$ or less. In particular, in the case of UVC, the control unit 50 maintains the daily irradiation amount to be 3 mJ/cm$^2$ or less. Further, in the case of UVA, when a daily irradiation time is less than 1,000 seconds, the daily irradiation amount is maintained such that the daily irradiation amount does not exceed 1 J/cm$^2$, and when the daily irradiation time is equal to or greater than 1,000 seconds, the daily irradiation amount is maintained such that the daily irradiation amount does not exceed 1 mW/cm$^2$.

In an embodiment of the present disclosure, the distance from the first and second light sources 30 and 40 to a target to be sterilized may be variously set. For example, the distance may vary depending on the intensities of light from the first and second light sources 30 and 40, the type of the target to be sterilized, an area or a volume to be sterilized, or a target material (for example, germs or bacteria) to be sterilized. Similarly, in an embodiment of the present disclosure, the time in which light from the first light source 30 and the second light source 40 is irradiated may be variously set.

Figure 3A:
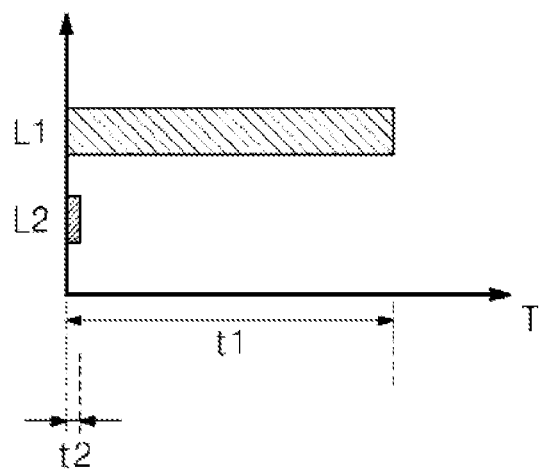
FIGS. 3A to 3C illustrate a method for driving a light radiation device, according to an embodiment of the present disclosure.
Figure 3B:
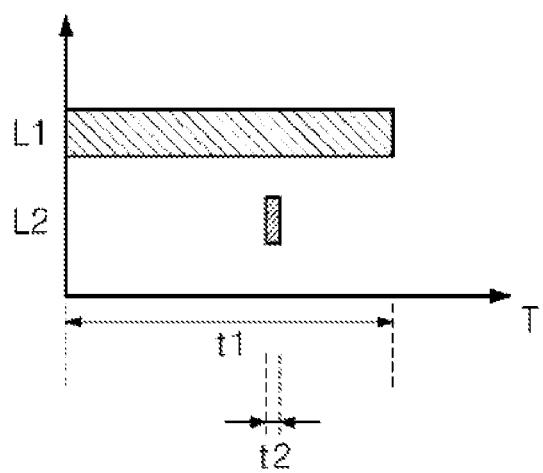
Figure 3C:
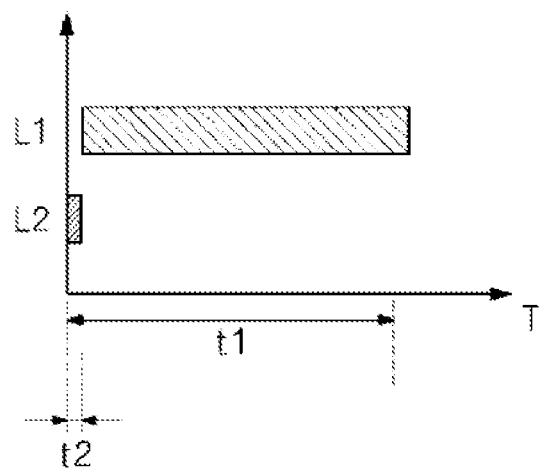

FIGS. 3A to 3C illustrate a method for driving a light radiation device, according to some embodiments of the present disclosure, and illustrates various timing based on turning on/off the first and second light sources;

In some embodiments, in the light radiation device 100, the first light from the first light source 30 is designated as "L1", the second light from the second light source 40 is designated as "L2", and an elapsed time is designated as "T". The first light source 30 is turned on for a first time t1 to emit the first light L1, and the second light source 40 is turned on for a second time t2 to emit the second light L2. In some embodiments, the first time t1 in which the first light L1 is irradiated may be longer than the second time t2 in which the second light L2 is irradiated. Since the second light L2 exerts a great influence on, especially, a human body, the second light L2 may be irradiated for a shorter time than the irradiation time of the first light L1. For example, the first light L1 may be applied for about 10 minutes, and the second light L2 may be applied for less than about 10 seconds.

The irradiation times t1 and t2 of the first light L1 and the second light L2 emitted from the first and second light sources 30 and 40, and amounts of the first light L1 and the second light L1 in irradiation may vary, but a total dose applied to the target to be sterilized may be set to a threshold value harmless to the human body. In particular, a predetermined dose per day, which is in a harmless range, may be an allowable dose when the second light L2 is applied to the human body, and then the second light source 40 may emit the second light L2 less than the allowable dose. The dose may vary depending on the harmfulness of the light emitted from the first light source 30 and the second light source 40. In some embodiments, the dose of the second light source 40 may be less than $1/10$ of the dose of the first light source 30. In other embodiments, the dose of the second light source 40 may be $1/20$ of the dose of the first light source 30. For example, the allowable dose of the second light L2 may be in the range of about 30 J/m$^2$ to about 1,000,000 J/m$^2$.

As illustrated in FIG. 3A and FIG. 3C, the first light L1 and the second light L2 may start to be irradiated simultaneously, or at mutually different times. When the first light L1 and the second light L2 may start to be irradiated at mutually different times, the first light L1 may be first irradiated, or alternatively, the second light L2 may be first irradiated. The times in which the first light L1 and the second light L2 are irradiated may overlap, or may not overlap. When the times, in which the first light L1 and the second light L2 are irradiated, do not overlap, the interval between the times in which the first light L1 and the second light L2 are applied may be set to be a shorter time interval. For example, the interval between the times in which the first light L1 and the second light L2 are applied may be within several hours, several minutes, or several seconds.

The sterilizing device according to some embodiments of the present disclosure exhibits a sterilization effect higher than the individual sterilization effect by the first light L1 or the individual sterilization effect by the second light L2, due to the synergy effect that may be obtained as the first light and the second light are applied simultaneously, or within the times close to each other.

In some embodiments, the sterilizing device employs the sterilization principle of the first light of generating reactive oxygen species due to a photosensitizer and the second light of causing the damage to DNA by obtaining a thymine dimer. In some embodiments, the significantly high sterilization effect may be obtained within a shorter time even with a smaller amount of energy by using both the first light source and the second light source, as compared to the case of an individual use of the first and second light sources.

The death rate of the bacteria having received chemical and physical stresses may rapidly increase even due to a weak stimulus additionally applied thereto. Accordingly, in some embodiments, mutually different two sterilizing mechanisms based on the first light and the second light, which correspond to blue light and UV light, apply mutually different stresses to the bacteria. Accordingly, the synergy effect of the stresses may destroy the bacteria with a smaller amount of energy as compared to the individual use of the two light sources. In some embodiments, the second light is irradiated in the amount harmless to a biological tissue of the target, which is to be sterilized, while being applied together with the first light. Accordingly, the sterilization synergy effect may be obtained by two light sources, so the present disclosure may produce the effective sterilization effect within a shorter time without the damage to a human tissue, when the target to be sterilized is a human body.

To the contrary, the use of only the first light is not harmful to the human body, but the sterilization power may be weak. Accordingly, the first light needs to be irradiated with higher energy for a longer time. The use of only the second light produces excellent sterilization power, but it may be harmful to the human body.

As described above, in some embodiments of the present disclosure, the sterilizing device may be used to sterilize various pathogens. Particularly, the light radiation device 100 may be used for sterilizing infectious bacteria in the initial stage by irradiating sterilizing light to an acute infected wound, and thus, the period for curing the wound may be short. For the acute wound, reducing an infectious bacteria count in the initial stage of the wound is the most important in the curing process of the acute wound. When the initial sterilization is not sufficiently performed with respect to the acute wound, the curing of the cut may not be fully perform. A cut may develop into a chronic cut that may not cured for 3 months or longer. However, when the infectious bacteria are sterilized in the initial stage using the light radiation device 100, the chronic cut may be prevented.

In addition, microorganisms, such as bacteria, germs, and moulds, present on animals and various articles may be sterilized in addition to the human body. Accordingly, the target to be sterilized by the sterilizing device according to an embodiment of the present disclosure is not limited to a human body, but it may apply to animals and various articles.

According to some embodiments of the present disclosure, as described above, the sterilization effect may significantly increase when both the first light and the second light emitted from the first light source 30 and the second light source 40 are applied simultaneously, or within the times close to each other. In addition, in some embodiments, when the first light and the second light are sequentially irradiated in that order, the significantly higher sterilization effect may be obtained as compared to the order that the second light and the first light are sequentially irradiated. Accordingly, the sterilization effect may be maximized through sequentially applying the first light, and then the second light to the target to be sterilized.

According to some embodiments of the present disclosure, the first light is applied to the target to be sterilized for a specific time before the second light is irradiated, and then the second light is irradiated. Accordingly, DNA is prevented from being recovered from the damage again after the first light is first irradiated. Accordingly, the significantly higher sterilization effect may be obtained even with a smaller dose as compared to the case that the first light is individually irradiated, i.e., without the irradiation of the second light. In addition, the second light may have excellent sterilization power for the subject to be sterilized but it may have an adverse effect on the human body, for example, skin aging or cancer, when the human body is exposed to the second light for a long time. Therefore, there may be limitations as to applying only the second light to the subject to be sterilized. However, according to embodiments of the present disclosure, the irradiation of the second light in addition to the irradiation of the first light may obtain the significant sterilization effect despite a small amount of the irradiation of the second light, in comparison with the irradiation of the second light alone.

In an embodiment of the present disclosure, when the second light is emitted sequentially after the first light, in addition to the first light, an amount of the second light needs to be controlled. In some embodiments, the synergy effect of sterilization may be obtained and an influence on the human body may be minimized by sequentially irradiating the first light and the second light. To this end, when the first light source 30 and the second light source 40 are turned on/off, one or more manner of continuously emitting light, one or more manner of sequentially increasing or decreasing the intensity of light, one or more flickering manner, or a manner of combining the above manners may be employed.

Figure 4A:
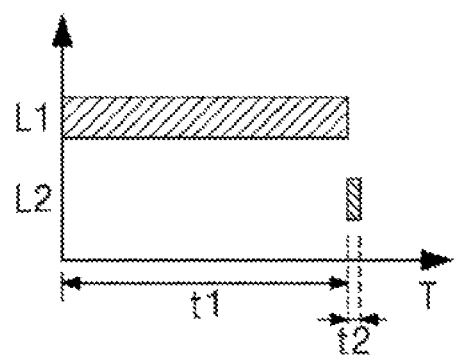
FIGS. 4A and 4B are views illustrating a method for driving a light radiation device, according to an embodiment of the present disclosure, when first light and second light are sequentially irradiated.
Figure 4B:
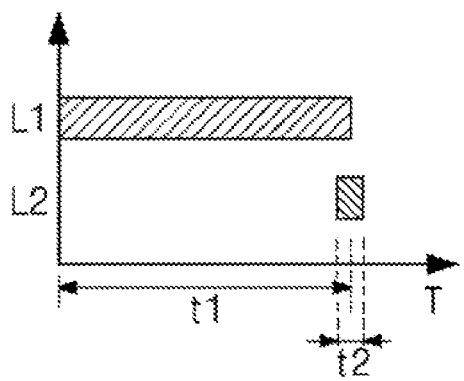

FIGS. 4A and 4B are views illustrating a method for driving the light radiation device according to embodiments of the present disclosure, when the first light and the second light are sequentially irradiated, and illustrates different times associated with turning on/off the first and the second light sources. The different times here may include different timings of emitting the first and second light sources, different durations of the irradiation of the first and the second light sources, etc.

Referring to FIGS. 4A and 4B, the first light L1 may be first irradiated, and then the second light L2 may be irradiated. When the first light L1 is first irradiated and then the second light L2 is irradiated, the sterilization effect may significantly increase as compared to the case that the second light is first irradiated and then the first light L1 is irradiated. When the second light L2 is first irradiated and the first light L1 is later irradiated, the effect of inhibiting the proliferation of bacteria by the second light L2 may be reduced. For example, even if the structure of DNA is partially mutated by the second light L2, the mutated DNA may be subject to photoreactivation by irradiating the first light L1. The bacteria recovered through the irradiation of the first light L1 return to a state in which the bacteria may be proliferated. Accordingly, although the total sterilization power is still excellent, the sterilization power in the final stage may be more reduced as compared to the case that the first light L1 and the second light L2 are sequentially irradiated.

Alternatively, when the first light L1 is applied to the target to be sterilized and then the second light L2 is sequentially applied to the target to be sterilized by using the light radiation device 100, reactive oxygen species are generated in bacteria by the first light L1, which is first irradiated, so oxidative stress is caused in bacteria. In this state, since additional sterilization is performed by the second light L2 irradiated later, the death rate of the bacteria may significantly increase even in a smaller irradiation amount.

In some embodiments, the time point at which the second light L2 is applied may vary in the setting that the first light L1 and the second light L2 are sequentially applied. For example, irradiation of the second light L2 may start after the irradiation of the first light L1 is finished as illustrated in FIG. 3A, and as illustrated in FIG. 3B, the irradiation of the second light L2 may start even though the irradiation of the first light L1 is not finished. In this case, since time points at which the first light L1 and the second light L2 are irradiated may partially overlap, the first time and the second time may have mutually overlap durations.

As described above, the light radiation device 100 according to embodiments of the present disclosure may be driven by the control unit 50 in the setting that the first light L1 and the second light L2 are sequentially irradiated.

Figure 5A:
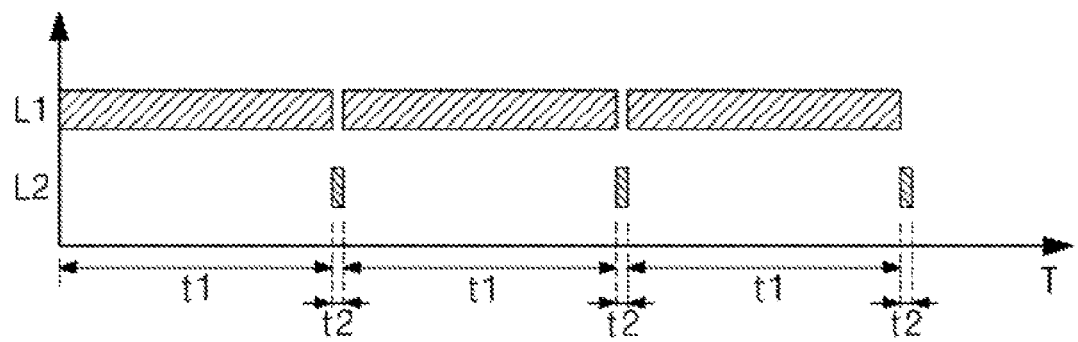
FIGS. 5A to 5C illustrate a method for driving a light radiation device, according to an embodiment of the present disclosure.
Figure 5B:
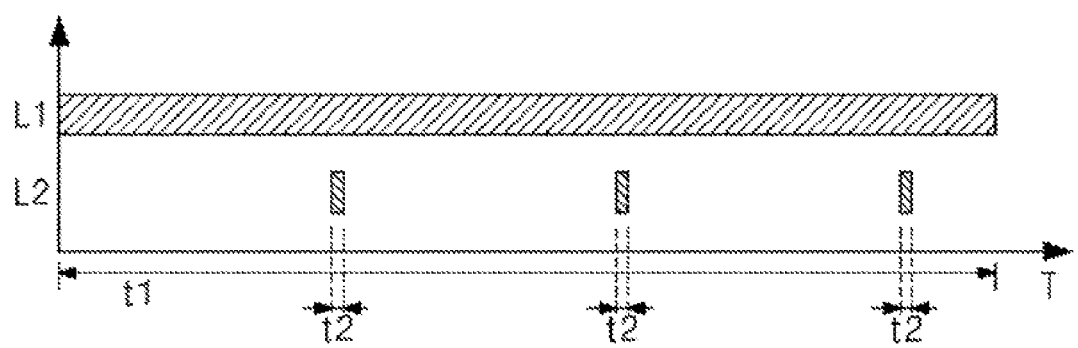
Figure 5C:
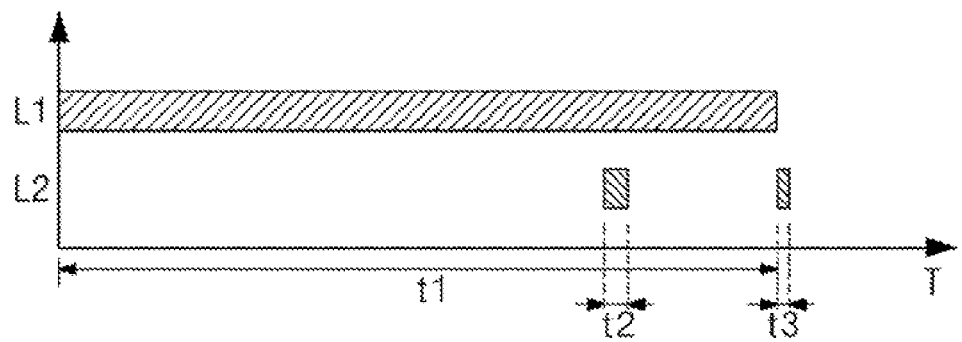

FIGS. 5A to 5C illustrate a method for driving a light radiation device, according to embodiments of the present disclosure, and illustrates different times associated with turning on/off the first and second light sources;

Referring to FIG. 5A, the first light L1 and the second light L2 may be periodically irradiated to the target to be sterilized. In other words, the first light L1 is irradiated to the target to be sterilized for the first time t1, and the second light L2 is irradiated to the target to be sterilized for the second time t2. Then, irradiation of the first light L1 and the second light L2 is repeated. The pattern of the repeat period and the repeat count may vary depending on the type of the target to be sterilized and the total amount of the target to be sterilized. In this case, the repeat period and the repeat count of the first light L1 and the second light L2 may be determined such that the total dose of the first light L1 and the total dose of the second light L2 become values equal to or less than the allowable dose for the human body in order to avoid harmful effects.

Referring to FIG. 5B, when the first light L1 and the second light L2 are applied, the first light L1 may be continuously applied to the target to be sterilized without interruption under the condition that the second light L2 is applied after the first light L1 is applied. To the contrary, the second light L2 is not continuously applied, but applied at intervals, and upon application, the second light L2 is superposed with the first light L1.

As illustrated in FIGS. 5A and 5B, the first light L1 may be continuously applied to the target to be sterilized for the first time t1 without interruption, and the second light L2 may be applied to the target to be sterilized for the second time t2 during the continuous application of the first light L1, after the first light L1 is applied to some extent. The second light L2 may be continuously repeatedly applied to the target to be sterilized.

Referring to FIG. 5C, when the first light L1 and the second light L2 are applied, the first light L1 may be continuously applied to the target to be sterilized without interruption or may be stopped before the second light L2 is applied, under the condition that the second light L2 is applied after the first light L1 is applied. As illustrated in FIG. 5C, when the first light L1 is applied to the target to be sterilized for the first time t1, the second light L2 may be applied for the second time t2 during the application of the first light L1. Thereafter, after the application of the first light L1 is finished, the second light L2 may be applied for a third time t3. In this case, regarding the application time of the second light L2, the second light L2 may be applied to the target to be sterilized for mutually different times within an allowable dose permitted as being safe for a human body. In other words, the second time t2 and the third time t3 in which the second light L2 is applied may have mutually different values, as shown in FIG. 5C.

In some embodiments of the present disclosure, when the second light L2 is applied as soon as the first light L1 is applied and stopped, the highest sterilization effect may be exhibited, and the second light L2 may be sequentially applied without interruption in the state the first light L1 is applied. However, instead of that the second light L2 is applied as soon as the first light L1 is applied and stopped, time may be slightly elapsed after the first light L1 is applied and stopped and then the second light L2 may be applied. In this case, the elapsed time interval may be significantly short. Meanwhile, when the sterilization effect is obtained as the first light L1 and the second light L2 are sequentially applied, the next sequential irradiation of the first light L1 and the second light L2 may be performed after a sufficient amount of time is elapsed.

In embodiments of the present disclosure, the first light source includes a blue wavelength sterilizable in the visible light wavelength band, but the first light source is not limited thereto. In other embodiments, the first light source may further include another light of the visible light wavelength band in addition to the blue wavelength band.

Figure 6:
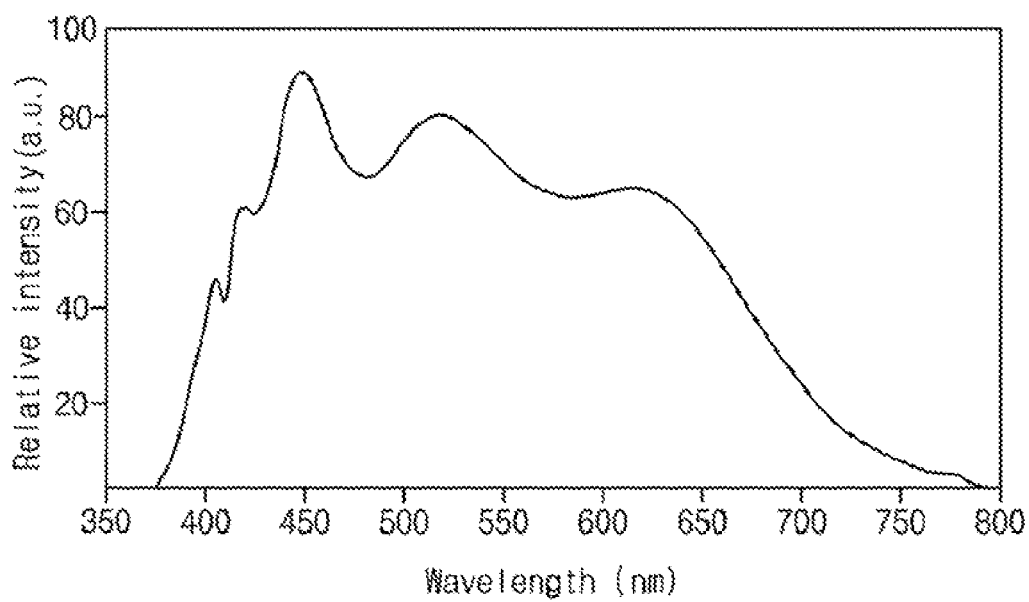
FIG. 6 is a spectrum of a light emitted from a first light source in a light emitting device according to an embodiment of the present disclosure.

FIG. 6 is a spectrum of a light emitted from a first light source in a light emitting device according to embodiments of the present disclosure.

Referring to FIG. 6, the first light source emits the light in a wavelength band of about 380 nm to about 750 nm, most of which corresponds to a visible light wavelength band. That is, the first light source corresponds to a light source which emits white light. In sine embodiments, the first light source includes a light in the blue wavelength band which is combined with the second light to generate synergy, and thus the above-described sterilization effect may be obtained in the same manner.

In addition, the first light source in the embodiment has a spectrum similar to sunlight having a form in which lights of the entire wavelength bands are evenly mixed. However, the first light source according to embodiments of the present disclosure is different from sunlight because the first light source emits a light except for the most of an ultraviolet wavelength band. The light source according to embodiments of the present disclosure emits a light having a wavelength band of about 380 nm to about 780 nm which substantially correspond to the entire wavelength band of a visible light.

In embodiments of the present disclosure, the phrase, "similar to sunlight" means that an overlapping area based on a normalized solar spectrum is more than a specific value and a deviation of the peak from the normalized solar spectrum (a deviation degree from the peak of the normalized solar spectrum) is lower than a specific value. For example, in an embodiment of the invention, the first light source may emit the light having an area of about 55% or more of an area of the normalized solar spectrum and a peak of the first light may have a deviation of about 0.14 or less from the normalized solar spectrum.

As described above, because the first light may have the spectrum similar to the sunlight, the first light may have an effect similar to an effect of frequent exposure to the sunlight. Therefore, synthesis of vitamin D may be facilitated or prevalence of diseases such as myopia may be lowered.

Figure 7A:
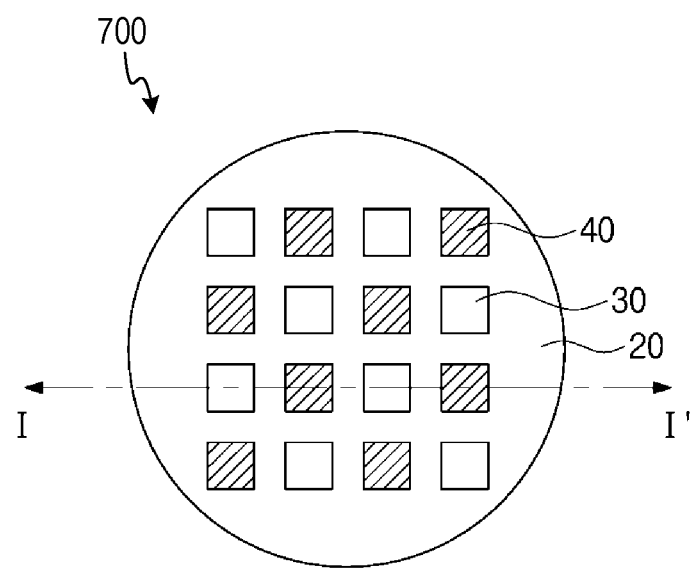
FIG. 7A is a plan view of the light radiation device 100 according to an embodiment of the present disclosure.

According to embodiments of the present disclosure, the light radiation device 100 may be implemented in various forms. FIG. 7A is a plan view of the light radiation device 100 according to embodiments of the present disclosure, and FIG. 7B is a sectional view taken along line I-I' of FIG. 7A.

Figure 7B:
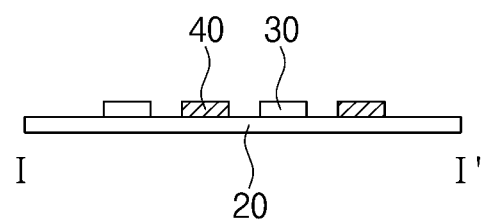
FIG. 7B is a sectional view taken along line I-I' of FIG. 7A.

Referring to FIGS. 7A and 7B, the light radiation device 100 may include the first light source 30, the second light source 40, and the substrate 20 on which the first light source 30 and the second light source 40 are mounted.

In some embodiments, a plurality of first light sources 30 may be provided, and a plurality of second light sources 40 may be provided. For example, the first light sources 30 and the second light sources 40 may be provided in equal numbers and may be alternately arranged in the form of a matrix as illustrated in FIG. 7A. However, numbers of the first and second light sources 30 and 40 is not limited thereto, and the number of the first light sources 30 may be smaller than the number of the second light sources 40. In addition, according to embodiments of the present disclosure, the first light sources 30 and the second light sources 40 may be regularly or irregularly arranged depending on the number of the first light sources 30 and the number of the second light sources 40.

According to embodiments of the present disclosure, the light radiation device 100 may further include a housing (not shown) to receive the first and second light sources 30 and 40 and the substrate 20. The housing may have a transmission window to transmit light emitted from the first and second light sources 30 and 40 and the light emitted from the first and second light sources 30 and 40 may be provided to the human body through the transmission window.

In an embodiment of the present disclosure, the control unit 50 (see FIG. 2) may be provided in various forms on the substrate 20. For example, the control unit 50 may be provided in the form of a separate circuit wiring or in the form of a separate chip, to be mounted on the substrate 20.

As described above, according to an embodiment of the present disclosure, the sterilizing device may be applied to various other devices requiring sterilizing, and particularly, may be applied to a device using a light source. In addition, the sterilizing device may be used as a lighting device in addition to the intrinsic function thereof (i.e., the sterilizing function). For example, according to an embodiment of the present disclosure, the sterilizing device may further include an additional light source for lighting a specific space. In this case, the additional light source may emit light in a visible wavelength band. The additional light source may emit light corresponding to the entire spectrum of the visible light area, or may emit light corresponding to the spectrum of a specific color.

Alternatively, in an embodiment of the present disclosure, the first light source 30 may emit light in the visible light wavelength band including light in the blue wavelength band without an additional light source. For example, the first light source 30 emits light in a wavelength band in the range of about 380 nm to about 750 nm, and most of the light corresponds to a visible light wavelength band. In this case, the first light source 30 may totally provide light in the visible light wavelength band while providing light in the blue wavelength band for obtaining a synergy effect through the combination with the second light source 40, thereby obtaining the sterilization effect as in embodiments described above. In this manner, when an additional light source is provided to emit light in the visible light wavelength band, or the first light source emits the light in the visible light wavelength band, the light may have the spectrum similar to that of sunlight. The light having the spectrum similar to that of sunlight may exhibit the effect similar to being frequently exposed to sunlight. Accordingly, the synthesis of vitamin D may be facilitated or the prevalence ratio of illnesses such as nearsightedness may be lowered.

Hereinafter, a specific embodiment of a lighting device according to an embodiment of the present disclosure will be described.

Figure 8:
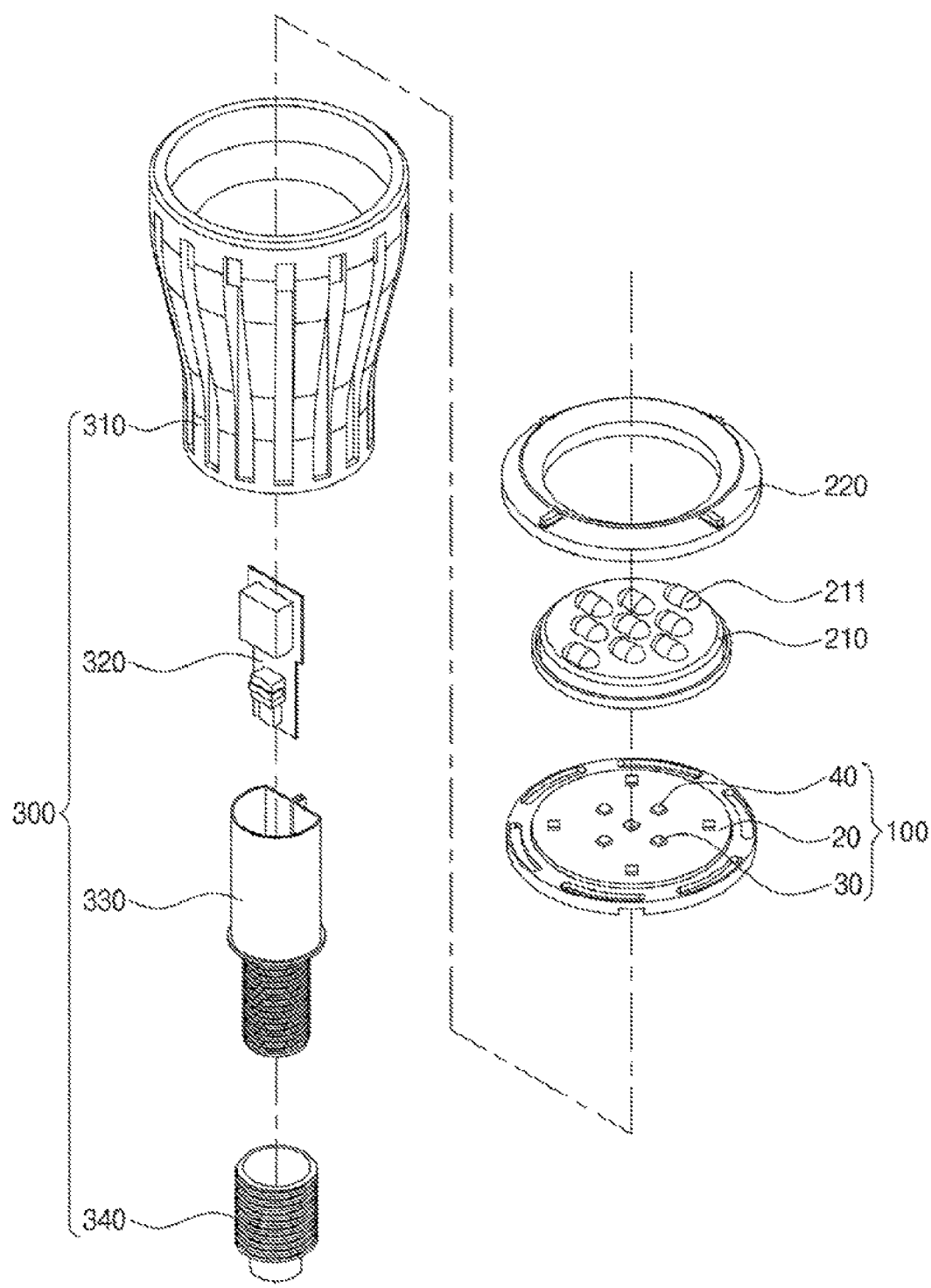
FIG. 8 illustrates an exploded view of a light device according to an embodiment of the present disclosure is implemented as a product.
Figure 9:
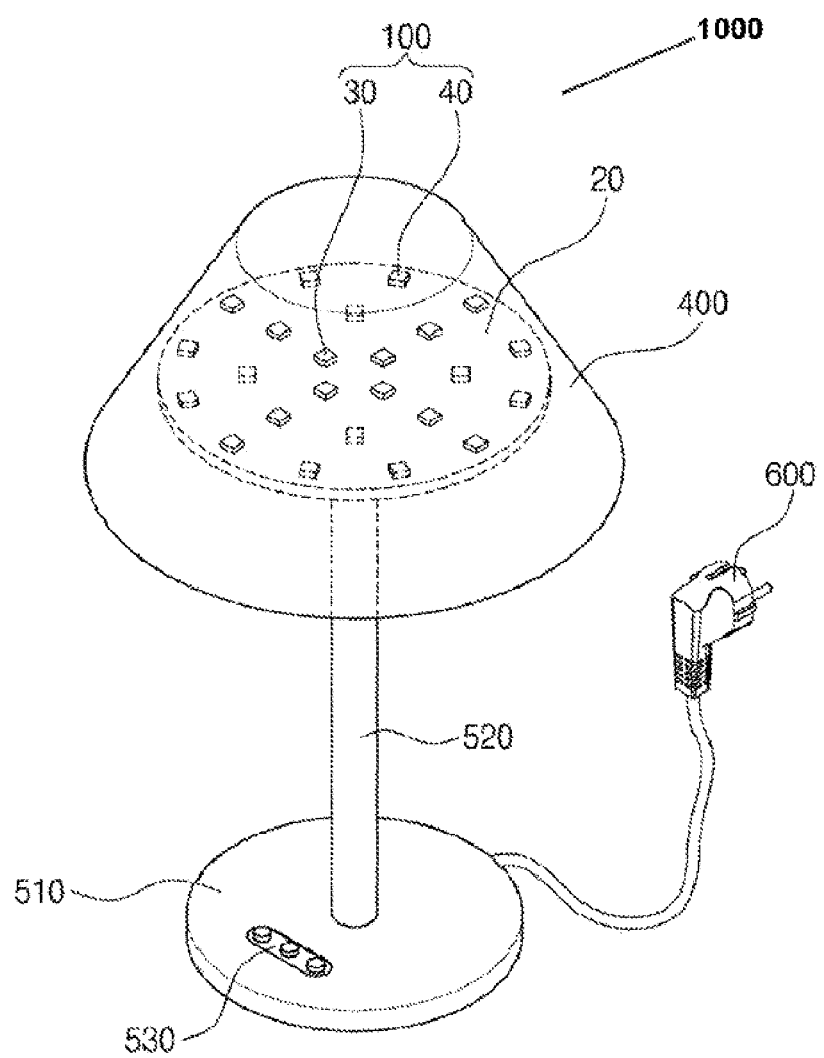
FIG. 9 illustrates an assembled view of a light device according to an embodiment of the present disclosure is implemented as a product.

FIGS. 8 and 9 illustrate an example in which a light device according to an embodiment of the present disclosure is implemented as a product.

Referring to FIG. 8, a lighting device according to an embodiment of the present disclosure includes the light emitting device 100 for emitting a light, a housing 300 in which the light emitting device 100 is accommodated, a window 210 provided at an upper part of the light emitting device, and a fixer 220 fixing the window 210 and the housing 300.

The housing 300 accommodates and supports the light emitting device 100 and is not limited as long as the housing 300 supplies electrical power to the light emitting device 100. For example, as shown, the housing 300 may include a main body 310, a power supplier 320, a power case 330, and a power connector 340. The power supplier 320 may be accommodated in the power case 330 and electrically connected to the light emitting device 100 and may include at least one IC chip. The IC chip may adjust, convert or control characteristics of the power supplied to the light emitting device 100.

The power case 330 may accommodate and support the power supplier 320, and the power case 330 in which the power supplier 320 is fixed may be located inside the main body 310.

The power connector 340 may be disposed at a lower end of the power case 330 and may be coupled with the power case 330. Accordingly, the power connector 340 may be electrically connected to the power supplier 320 inside the power case 330 to serve as a path through which external power is supplied to the power supplier 320.

The light emitting device 100 may include the substrate 20 and the first and second light sources 30 and 40 disposed on the substrate 20 and may have a form as the above-described embodiments. The light emitting device 100 may be provided on the upper part of the main body 310 and electrically connected to the power supplier 320. The substrate 20 may have a shape corresponding to the fixer 220 of the upper part of the main body 310 to be stably fixed to the main body 310.

The window 210 may be disposed on the housing 300 to cover the upper part of the light emitting device 100. The window 210 may be disposed on the light emitting device 100 and may be fixed to the main body 310 to cover the light emitting device 100. The window 210 may be provided with a lens member 211 to facilitate diffusion of the light from the light emitting device 100. The window 210 may have a transparent material. A shape and light transmittance of the window 210 may be modified to adjust directivity of the lighting device. Therefore, the window 210 may be modified in various forms depending on the purpose of use and application of the lighting device.

The fixer 220 may be provided on the window 210 to fasten the window 210, the light emitting device 100, and the main body 310 to one another.

The lighting device having the above-described structure may be mounted in various light treatment devices. In addition, the lighting device may be used as a lighting fixture mounted on a wall or a ceiling forming a specific space (e.g., a chamber).

The lighting device according to an embodiment of the present disclosure may be implemented in a form which is used in real life.

Referring to FIG. 9, the lighting apparatus according to another embodiment of the present disclosure may include a pedestal 510, the light emitting device 100 for emitting the light, a supporter 520, and a reflector 400 surrounding the light emitting device 100. The lighting device 1000' according to another embodiment of the present disclosure may be disposed on a variety of treatment devices.

An input unit 530 may be disposed on a surface of the pedestal 510 to control an operation of the lighting device 1000'. The pedestal 510 is connected and fixed through the substrate 20 on which the lighting device 100 is disposed and the supporter 520. The pedestal 510 allows power to be supplied to the light emitting device through a power supplier 600. The supporter 520 may be connected between the pedestal 510 and the substrate 20 on which the light emitting device 100 is disposed and a wire (not shown) for supplying the power may be provided therein.

In the embodiment, the supporter 520 is shown as being formed of a single solid material, but is not limited thereto, and may be made of a bendable material capable of bending at least one time or made of a flexible material to be changed into various shapes. For example, the supporter 520 may have a ductility to be deformed by a specific degree of external force and maintain a shape the supporter 520 when there is no external force. For example, a wiring may receive an external force to be partially changed and the changed wiring may maintain the final shape to which the external force is applied when the external force is removed. To this end, the supporter 520 may be provided in a bellows shape.

The reflector 400 surrounding the light emitting device 100 may be made of a metallic material such as aluminum or the like, which is capable of reflecting a light emitted from the light emitting device and increasing illuminance, or a material capable of transmitting a light. A coating layer including a photocatalyst material may be formed on an inner surface of the reflector 400. The photocatalyst material may include at least one selected from the group of $TiO_2$, $ZnO$, $ZrO_2$, and $WO_3$.

Hereinafter, an experimental example of the sterilization effect of the light radiation device according to an embodiment of the present disclosure will be described.

Experimental Example 1—Sterilization Effect According to Irradiation Conditions

FIG. 10 is a graph illustrating a sterilization effect depending on irradiation conditions when a light is irradiated to a sterilization subject using a conventional light emitting device and a light emitting device according to an embodiment of the present disclosure. In FIG. 10, a bacterium used as a subject of sterilization is *Staphylococcus aureus*. The *Staphylococcus aureus* was smeared on a bacterial culture medium and incubated at 35 to 37° C. for one day, and bacterial colonies formed on the bacterial culture medium were collected, suspended in a saline solution, and performed with centrifuge, and a supernatant was discarded, a saline solution is added to be diluted, and thus a bacterial solution having a suitable concentration for a sterilization experiment was prepared. The prepared bacterial solution was placed in separate containers, the conventional light emitting device and the light emitting device according to an embodiment of the present disclosure were installed at a specific distance from the containers, and then lights were sequentially irradiated. Thereafter, the bacterial solutions irradiated with the lights were diluted, applied evenly bacterial culture media, and incubated for one day at 35 to 37° C. Colonies formed on the bacterial culture media were checked, multiplied by a dilution factor, and counted. Therefore, the results for sterilization effects were obtained.

In FIG. 10, an x-axis shows doses of the first and second lights and a y-axis shows degree of inactivation of bacteria on a logarithmic scale. In Comparative Example 1, only the second light of 275 nm wavelength band was applied to the bacteria. In Comparative Example 2, only the first light of 405 nm wavelength band was applied to the bacteria. In Comparative Example 3, the first light of the 405 nm wavelength band was applied to the bacteria after the second light of the 275 nm wavelength band. In Example, the second light of the 275 nm wavelength band was applied to the bacteria after the first light of the 405 nm wavelength band was applied. Meanwhile, in the graph, in Comparative Example 1, the second light of the wavelength band of 275 nm was applied only with a dose of 3 $mJ/cm^2$, and in Comparative Example 2, Comparative Example 3, and Example, respectively, the first light of the wavelength band of 405 nm was applied and changed at doses of 30 $mJ/cm^2$, 60 $mJ/cm^2$, 90 $mJ/cm^2$, 120 $mJ/cm^2$, and 150 $mJ/cm^2$, respectively and the second light of the wavelength band of 275 nm was applied with a dose of 30 $mJ/cm^2$. Here, in the case of the second light, the dose is set lower than that of the first light in consideration of the allowable dose to the human body.

Referring to FIG. 10, when only the second light was applied to the bacteria at a dose of 3 mJ/cm² in Comparative Example 1, the degree of inactivation was about 1.5 log CFU/ml. When only the first light was applied to the bacteria at a dose of 30 mJ/cm² in Comparative Example 2, the degree of inactivation was about 1 log CFU/ml. When the second light was pre-irradiated with the bacteria at a dose of 3 mJ/cm² and the first light was post-irradiated with a dose of 30 mJ/cm², the degree of inactivation was about 1.5 log CFU/ml. However, in the embodiment in which the first light was irradiated with a dose of 30 mJ/cm² and the second light was irradiated with a dose of 3 mJ/cm², the deactivation degree was about 4 log CFU/ml and the sterilization effect was very high. Here, in Comparative Example 3 and Example, the order of irradiation of the first light and the second light were different but the same dose was irradiated to the bacteria. It was seen that the actual sterilization degree showed a significant difference in effect.

In addition, in Comparative Example 2, Comparative Example 3, and Example, the first light of a dose of 60 mJ/cm² were applied. The sterilization effect of Example was significantly higher than Comparative Example 2, or Comparative Example 3.

Meanwhile, when the dose of the first light was more than 90 J/cm², Comparative Example 3 and Example showed a stagnant value of about 6 log CFU/ml. This is because there are no more bacteria to be sterilized under laboratory conditions without introduction of new bacteria. Accordingly, it may be expected that the sterilization effect of Example will be significantly higher than the sterilization effect of Comparative Examples 1 to 3 under open external conditions in which new bacteria are continuously introduced.

Table 1 below shows a minimum dose in order to obtain a desired degree of sterilization in Comparative Examples 1 to 3 and Example. Here, in Comparative Example 1, only the second light of 275 nm wavelength band was applied to the bacteria. In Comparative Example 2, only the first light of 405 nm wavelength band was applied to the bacteria. In Comparative Example 3, the first light of the 405 nm wavelength band was applied to the bacteria after the second light of the 275 nm wavelength band. In Example, the second light of the 275 nm wavelength band was applied to the bacteria after the first light of the 405 nm wavelength band was applied.

Referring to Table 1, in the case of Comparative Example 1 using the second light source alone, a sterilization effect of 90% or more, 99% or more, or 99.9% or more even might be obtained with a very small dose. However, since the influence on the human body is large in the case of the second light, it is difficult to proceed with sterilization by only raising a dose of the second light.

Next, in Comparative Example 2, Comparative Example 3 and Example using a combination of the first light and the second light, it was seen that Example had higher sterilization effect with a very small dose of the first light in comparison with those of Comparative Example 2 and Comparative Example 3. For example, in order to obtain a sterilization effect of 99%, a dose of 65 J/cm² was required for Comparative Example 2 and a dose of 40 J/cm² was required for Comparative Example 3, whereas only a dose of 15 J/cm2 was required for Example.

TABLE 1

| Sterilization performance | Example | Comparative Example 1 | Comparative Example 2 | Comparative Example 3 |
| --- | --- | --- | --- | --- |
| 1 log sterilization (90% sterilization) | 7 J/cm² ±10% | 2 mJ/cm² ±10% | 30 J/cm² ±10% | 20 J/cm² ±10% |
| 2 log sterilization (99% sterilization) | 15 J/cm² ±10% | 4 mJ/cm² ±10% | 65 J/cm² ±10% | 40 J/cm² ±10% |
| 3 log sterilization (99.9% sterilization) | 25 J/cm² ±10% | 8 mJ/cm² ±10% | 110 J/cm² ±10% | 60 J/cm² ±10% |

As described above, it was seen that the light emitting device according to the embodiments of the present disclosure exhibited a significantly higher sterilization effect than the conventional light emitting device such as Comparative Example 1, Example 2, and Example 3.

Experimental Example 2—Individual Sterilization Power Test of the First Light and the Second Light In the present test, an MRSA strain was used as a pathogen. After the MRSA strain was cultured, a suspension having a constant bacteria concentration (7 log) was prepared. The first light and the second light were irradiated to the bacteria suspension in each light amount. In this case, the wavelength of the first light was 405 nm and the wavelength of the second light was 275 nm. The bacteria irradiated with the first light and the second light were each diluted at a specific concentration, inoculated into agar plates, and then cultured again. Thereafter, the number of colonies of the cultured bacteria was identified, and the numerical value was converted into a log value. Each test was performed under the same conditions five times.

Figure 11A:
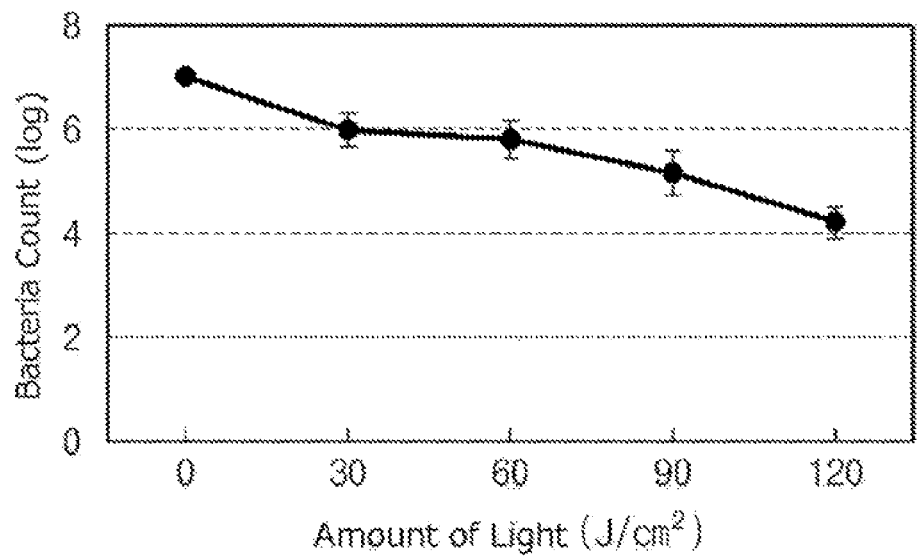
FIG. 11A is a graph illustrating a test result of sterilization power of first light.
Figure 11B:
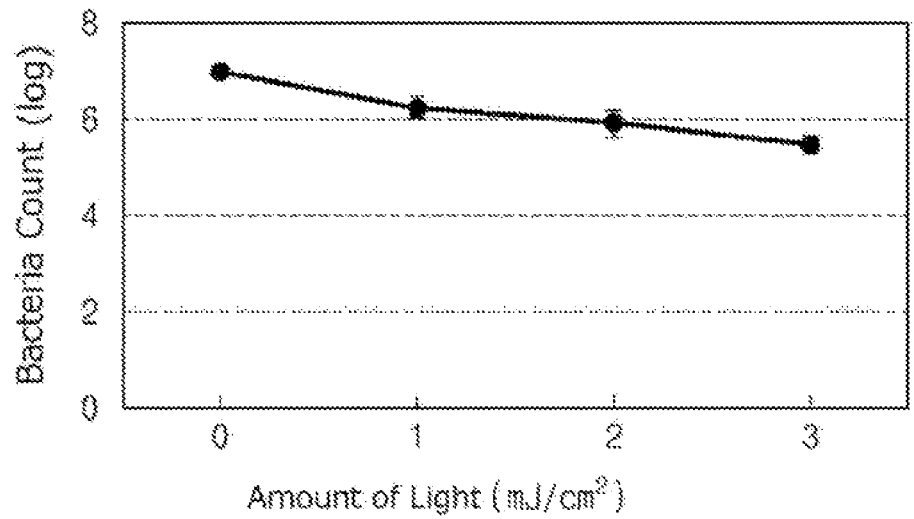
FIG. 11B is a graph illustrating a test result of sterilization power of second light.

Table 2 and FIG. 11A illustrate the test result for the sterilization power of the first light, and Table 3 and FIG. 11B illustrate the test result for the sterilization power of the second light.

TABLE 2

| Light amount (J/cm²) | 0 | 30 | 60 | 90 | 120 |
| --- | --- | --- | --- | --- | --- |
| Bacteria Count | 7.00 | 5.97 | 5.78 | 5.15 | 4.17 |
| Error | 0.00 | 0.32 | 0.35 | 0.43 | 0.29 |

It may be recognized from Table 2 and FIG. 11A that, as an amount of the first light, which is irradiated, is increased, the bacteria count is reduced. It is clear that the bacteria count is reduced even if the margin of error is considered.

TABLE 3

| Light amount (J/cm²) | 0 | 1 | 2 | 3 |
| --- | --- | --- | --- | --- |
| Bacteria Count | 7.00 | 6.23 | 5.88 | 5.45 |
| Error | 0.00 | 0.23 | 0.27 | 0.18 |

It may be recognized from Table 3 and FIG. 11B that, as an amount of the second light, which is irradiated, is increased, the bacteria count is reduced. It is clear that the bacteria count is reduced even if the margin of error is considered. In addition, it is recognized that the second light sterilizes the bacteria with an amount smaller than an amount of the first light.

Experimental Example 3—Sterilization Power Test in the Combination of the First Light and the Second Light In the present test, an MRSA strain was used as a pathogen. After the MRSA strain was cultured, a suspension having a constant bacteria concentration (7 log) was prepared. The individual irradiation of the first light, the individual irradiation of the second light, and the combination of the first light and the second light were performed with respect to the bacteria suspension. Comparative Example 1 illustrates that non-light is irradiated to the bacteria suspension, Comparative example 2 illustrates that the second light was individually irradiated to the bacteria suspension, Comparative example 3 illustrates that the first light was individually irradiated to the bacteria suspension, and Embodiment illustrates that the combination of the first light and the second light was irradiated to the bacteria suspension. In this case, the wavelength of the first light was 405 nm, the dose of the first light was 120 J/cm$^2$, and the wavelength of the second light was 275 nm, and the dose of the second light was 3 mJ/cm$^2$. In Embodiment, the second light was irradiated in the dose of 3 mJ/cm$^2$ and then the first light was irradiated in the dose of 120 J/cm$^2$. Next, in Comparative Examples 1 to 3 and Embodiment, the bacteria were diluted at a constant concentration, inoculated into agar plates, and then cultured again. Thereafter, the number of colonies of the cultured bacteria was identified, and the numerical value was converted into a log value.

Each test was performed under the same conditions five times.

Figure 12A:
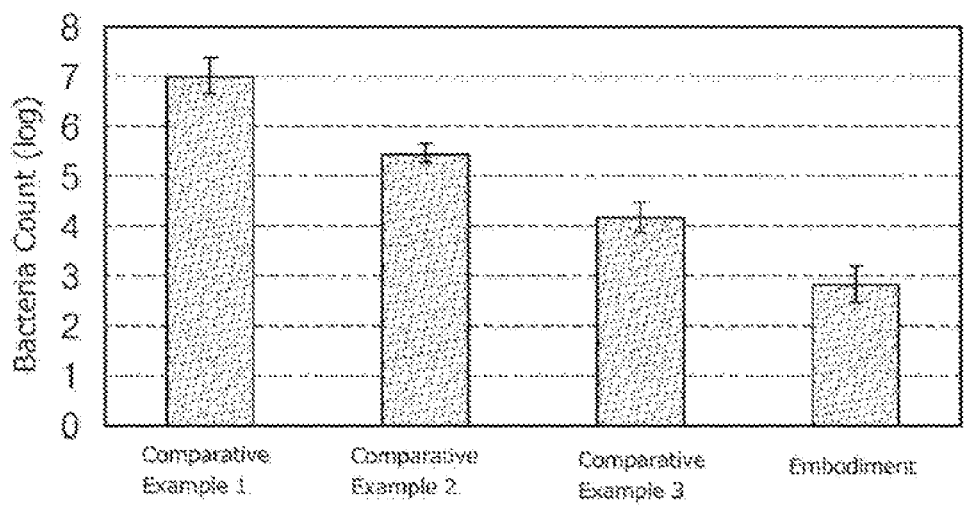
FIG. 12A illustrates a bacteria count when first light is individually irradiated, when second light is individually irradiated, and when both the first light and the second light combined are irradiated.
Figure 12B:
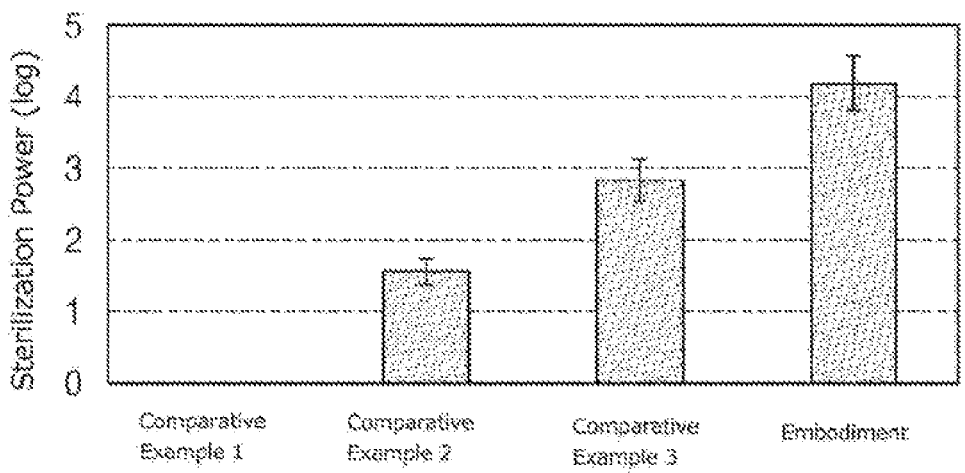
FIG. 12B illustrates sterilization power when first light is individually irradiated, when second light is individually irradiated, and when both the first light and the second light combined are irradiated.

FIG. 12A and Table 4 illustrate the bacteria count in the individual irradiation of the first light, the individual irradiation of the second light, and the irradiation of the combination of the first light and the second light. FIG. 12B and Table 5 illustrate the sterilization power in the individual irradiation of the first light, the individual irradiation of the second light, and the irradiation of the combination of the first light and the second light.

TABLE 4

| Light condition | Comparative Example 1 | Comparative Example 2 | Comparative Example 3 | Embodiment |
|---|---|---|---|---|
| Bacteria Count | 7.00 | 5.45 | 4.17 | 2.83 |
| Error | 0.00 | 0.18 | 0.29 | 0.37 |

TABLE 5

| Light condition | Comparative Example 1 | Comparative Example 2 | Comparative Example 3 | Embodiment |
|---|---|---|---|---|
| Sterilization power | 0.00 | 1.55 | 2.83 | 4.17 |
| Error | 0.00 | 0.18 | 0.29 | 0.37 |

Referring to FIGS. 12A, 12B, Table 4, and Table 5, about 90% of sterilization power was illustrated in the individual irradiation of the second light, about 99% of sterilization power was illustrated in the individual irradiation of the first light, and 99.99% or more of sterilization power was illustrated in irradiation of the combination of the first light and the second light. Accordingly, it may be recognized that an amount of bacteria is significantly reduced, and thus the sterilization power is significantly increased when the combination of the first light and the second light is irradiated, as compared to when the light is not irradiated, and to when the first light or the second light is individually irradiated.

Experimental Example 4-Test for Variation in Sterilization Power Based on Sequence of Combining the First Light and the Second Light In the present test, an MRSA strain was used as a pathogen. After the MRSA strain was cultured, a suspension having a constant bacteria concentration (7 log) was prepared. After the second light was irradiated to the bacteria suspension, the first light was irradiated to the bacteria suspension. In addition, the second light was irradiated to the bacteria suspension after the first light was irradiated to the bacterial suspension. Comparative example 1 illustrates that non-light was irradiated to the bacteria suspension, Embodiment 1 illustrates that the first light was irradiated to the bacteria suspension after the second light was irradiated to the bacteria suspension, and Embodiment 2 illustrates that the second light was irradiated to the bacteria suspension after the first light was irradiated to the bacteria suspension.

In Embodiment 1, after the second light having the wavelength of 275 nm was irradiated to the bacteria suspension with a dose of 3 mJ/cm$^2$, the first light having the wavelength of 405 nm was irradiated to the bacteria suspension with a dose of 120 J/cm$^2$. In Embodiment 2, after the first light having the wavelength of 405 nm was irradiated to the bacteria suspension with a dose of 120 J/cm$^2$, the second light having the wavelength of 275 nm was irradiated with the dose of 3 mJ/cm$^2$.

Next, in Comparative Example, Embodiment 1, and Embodiment 2, the bacteria were diluted at a constant concentration, inoculated into agar plates, and then cultured again. Thereafter, the number of colonies of the cultured bacteria was identified, and the numerical value was converted into a log value.

Each test was performed under the same conditions five times.

Figure 13A:
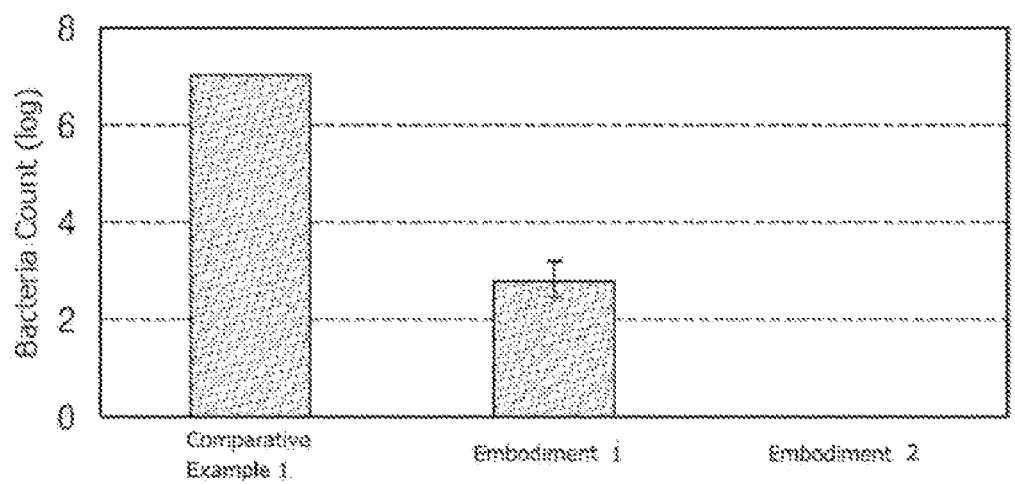
FIG. 13A illustrates a bacteria count irradiated with light obtained by differently setting the sequence of combining first light and second light.
Figure 13B:
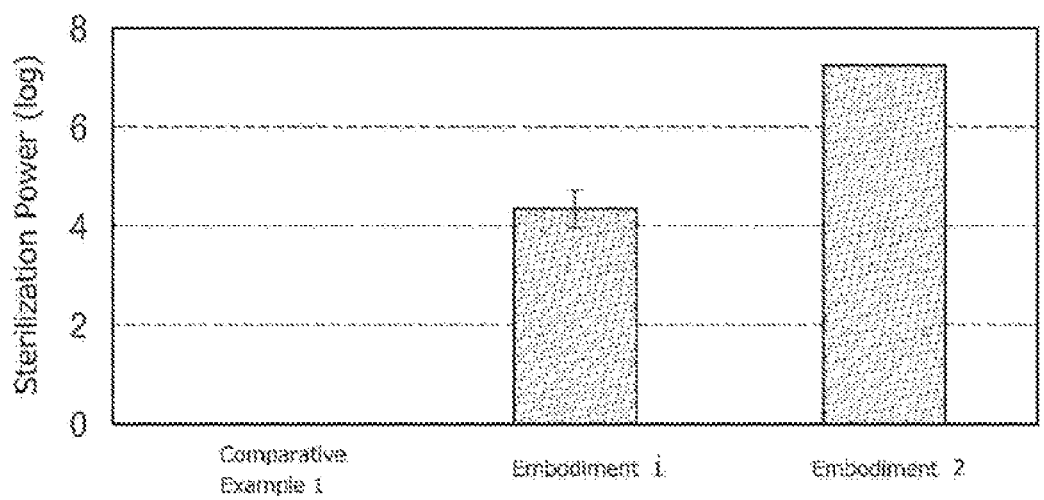
FIG. 13B illustrates sterilization power obtained by differently setting the sequence of combining the first light and the second light.

FIG. 13A and Table 6 illustrate the bacteria count when the sequence of combining the first light and the second light is differently set, and FIG. 13B and Table 7 illustrate the sterilization power when the sequence of combining the first light and the second light is differently set.

TABLE 6

| Light condition | Comparative Example | Embodiment 1 | Embodiment 2 |
|---|---|---|---|
| Bacteria Count | 7.00 | 2.83 | 0.00 |
| Error | 0.00 | 0.37 | 0.00 |

TABLE 7

| Light condition | Comparative Example | Embodiment 1 | Embodiment 2 |
|---|---|---|---|
| Sterilization power | 0.00 | 4.17 | 7.00 |
| Error | 0.00 | 0.37 | 0.00 |

It may be recognized from FIGS. 13A, 13B, Table 6, and Table 7 that Embodiment 1 illustrates 99.99% of sterilization power, and bacteria are not observed in Embodiment 2, so the sterilization is substantially completely achieved.

In other words, the case that the second light is irradiated after the first light is irradiated shows significantly higher sterilization power with the same irradiation amount of light, as compared to the case the first light is irradiated after the second light is irradiated, which means that the same sterilization power is obtained with a smaller amount of light as compared to the case the first light is irradiated after the second light is irradiated. The application of a smaller amount of light means the reduction in the light irradiation time. Accordingly, Embodiment 2 is more reduced in the light irradiation time than Embodiment 1.

Experimental Example 5—Setting Condition of an Amount of Light (In Vitro)

The bacteria count and the sterilization power were measured as function of an amount of light in vitro condition when the first light and the second light are sequentially irradiated, in order to find out the optimal amount of each light, based on that the sequential irradiation of the first light and the second light, which shows the increase in the sterilization power.

In the present test, an MRSA strain was used as a pathogen. After the MRSA strain was cultured, a suspension having a constant bacteria concentration (7 log) was prepared. The first light and the second light were sequentially irradiated to the bacteria suspension by changing the dose of the first light to 30 J/cm², 60 J/cm², 90 J/cm², and 120 J/cm². However, in the case of the second light, the light of 275 nm was employed with a dose limited to 3 mJ/cm² based on the allowable level of the human body.

Next, the bacteria were diluted at a constant concentration, inoculated into agar plates, and then cultured again. Thereafter, the number of colonies of the cultured bacteria was identified, and the numerical value was converted into a log value.

Each test was performed under the same conditions five times.

Figure 14A:
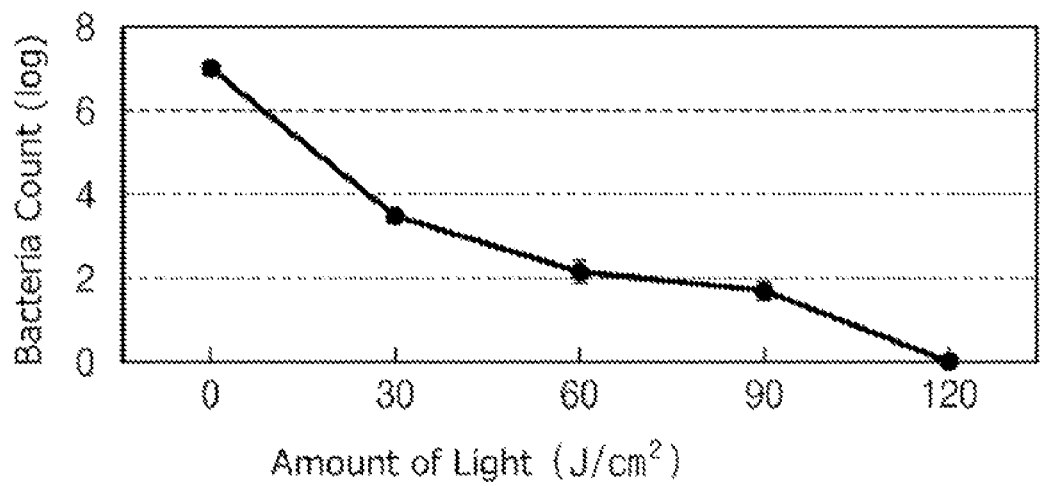
FIG. 14A illustrates a bacteria count as a function of an amount of the first light under in vitro condition when first light and second light were sequentially irradiated.
Figure 14B:
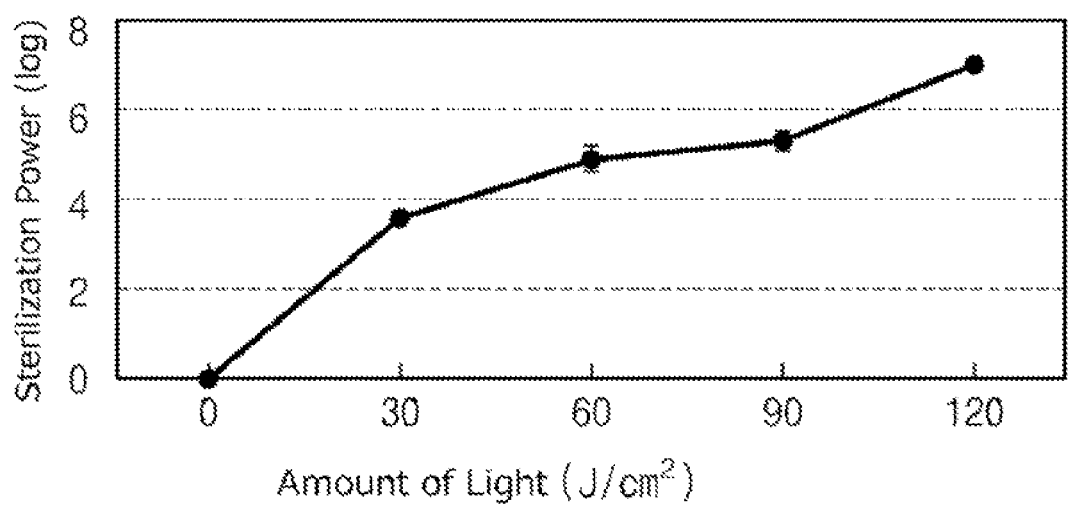
FIG. 14B illustrates sterilization power as a function of the amount of the first light under in vitro condition when the first light and the second light were sequentially.

FIG. 14A and Table 8 show the bacteria count when an amount of the first light is variably set while the first light and the second light are sequentially irradiated, and FIG. 14B and Table 9 show the sterilization power when an amount of the first light is variably set while the first light and the second light are sequentially irradiated.

TABLE 8

| Light amount (J/cm²) | 0 | 30 | 60 | 90 | 120 |
|---|---|---|---|---|---|
| The number of bacteria | 7.00 | 3.47 | 2.13 | 1.70 | 0.00 |
| Error | 0.00 | 0.13 | 0.27 | 0.22 | 0.00 |

TABLE 9

| Light amount (J/cm²) | 0 | 30 | 60 | 90 | 120 |
|---|---|---|---|---|---|
| Sterilization power | 0.00 | 3.53 | 4.87 | 5.03 | 7.00 |
| Error | 0.00 | 0.13 | 0.27 | 0.22 | 0.00 |

It may be recognized from FIGS. 14A, 14B, Table 8, and Table 9 that the number of bacteria is reduced as an amount of the first light is increased and the sterilized is completely achieved with a dose of 120 J/cm².

Experimental Example 6—Setting of Light Amount Condition (In Vivo)

It was recognized through Embodiment 4 that the sterilization is completely achieved when a dose of the first light (having the wavelength of 275 nm) is 120 J/cm², under the condition that the dose of the second light (having the wavelength of 405 nm) is 3 mJ/cm². Accordingly, the test was performed to determine whether the above sterilization effect is obtained under in vivo condition.

The present test was performed using a mouse to determine whether the application of light is effective and safe under in vivo condition. The condition for an amount of light is set to the same condition as that in vitro. For a mouse, a BALB/c mouse (6-8 weeks old) was used, the back of the mouse was shaved, and then a cut was formed in the diameter of 10 mm in the back of the mouse. After the pathogenic bacteria was inoculated (at 5 log) on the wound, the first light and the second light were sequentially irradiated by changing the dose of the first light to 30 J/cm², 60 J/cm2, 90 J/cm2, and 120 J/cm2. However, in the case of the second light, the light of 275 nm was employed with a dose limited to 3 mJ/cm² based on the allowable level of the human body. Next, tissues were sampled, and the sampled tissues were disrupted, diluted at a predetermined concentration, inoculated on agar plates, and then cultured again. Thereafter, the number of colonies of the cultured bacteria was identified, and the numerical value was converted into a log value.

Each test was performed under the same conditions five times.

Figure 15A:
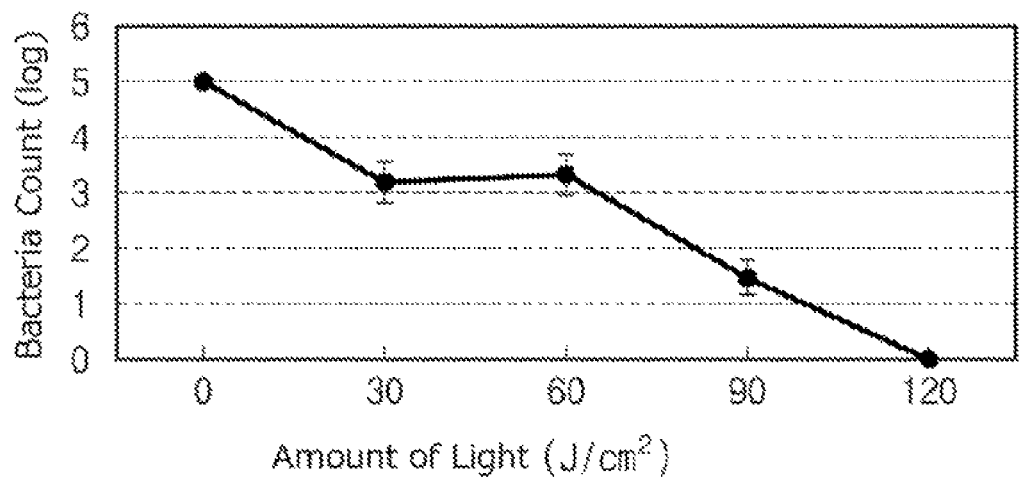
FIG. 15A illustrates a bacteria count as a function of an amount of the first light under in vivo condition, when first light and second light were sequentially irradiated.
Figure 15B:
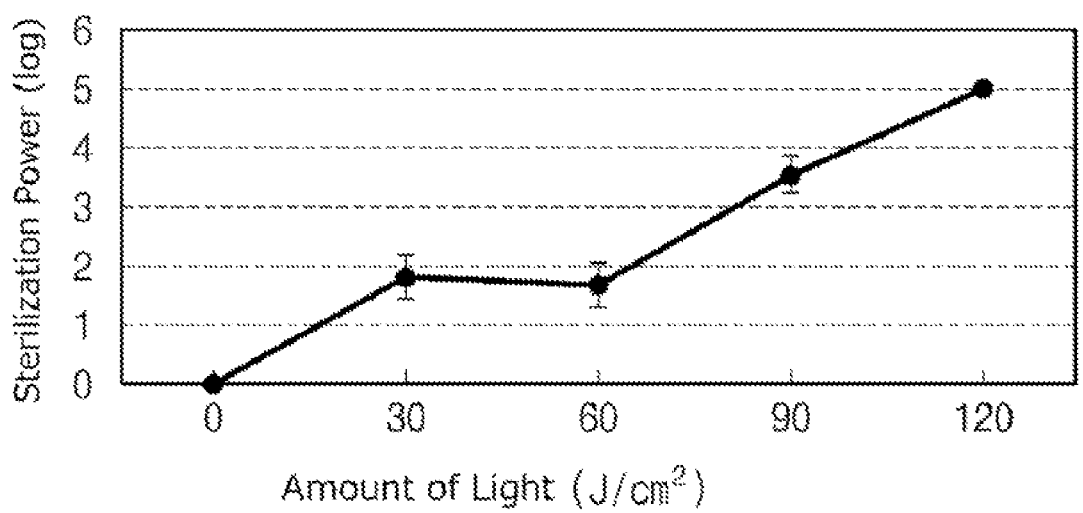
FIG. 15B illustrates the sterilization power as a function of an amount of the first light under in vivo condition, when the first light and the second light were sequentially irradiated.

FIG. 15A and Table 10 show the bacteria count as a function of an amount of the first light, when the first light and the second light were sequentially irradiated. FIG. 15B and Table 11 show the sterilization power as a function of an amount of the first light, when the first light and the second light were sequentially irradiated.

TABLE 12

| Light amount (J/cm²) | 0 | 30 | 60 | 90 | 120 |
|---|---|---|---|---|---|
| Bacteria Count | 5.00 | 3.17 | 3.32 | 1.48 | 0.00 |
| Error | 0.00 | 0.36 | 0.38 | 0.31 | 0.00 |

TABLE 13

| Light amount (J/cm²) | 0 | 30 | 60 | 90 | 120 |
|---|---|---|---|---|---|
| Sterilization power | 0.00 | 1.83 | 1.68 | 3.52 | 5.00 |
| Error | 0.00 | 0.36 | 0.38 | 0.31 | 0.00 |

It may be recognized from FIGS. 15A, 15, Table 10, and Table 11 that the bacteria count is reduced as an amount of the first light is increased under in vivo condition and the sterilized is completely achieved with a dose of 120 J/cm².

Experimental Example 7—Effectiveness Evaluation 1 (In Vivo)

In embodiment 5, a dose of light for sterilization was recognized under in vivo condition, and the variation in the sterilization power and the variation in the bacteria count as functions of time were tested under in vivo condition.

The present test was performed using a mouse. For the mouse, a BALB/c mouse (6-8 weeks old) was used, the back of the mouse was shaved, and then a cut was formed in the diameter of 10 mm in the back of the mouse. After the pathogenic bacteria was inoculated (at 5 log) on the wound, the first light and the second light were sequentially irradiated and repeatedly irradiated six times in total at the same time every day while a dose of the first light (having the wavelength of 405 nm) is 120 J/cm². In the case of the second light, the light of 275 nm was employed with a dose limited to 3 mJ/cm² based on the allowable level of the human body.

Next, to determine the bacteria count every day, tissues were sampled, and the sampled tissues were disrupted, diluted at a predetermined concentration, inoculated on agar plates, and then cultured again. Thereafter, the number of colonies of the cultured bacteria was identified, and the numerical value was converted into a log value. To determine the initial sterilization power, the bacteria count was detected until three-time light irradiation.

Figure 16:
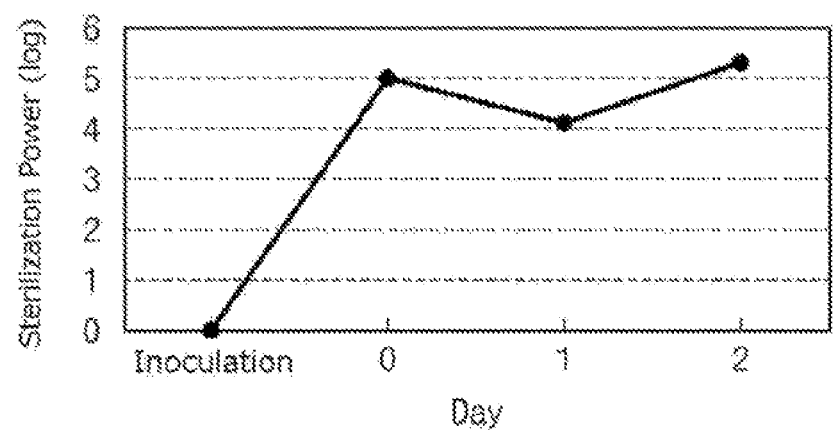
FIG. 16 is a graph illustrating the variation in sterilization power based on days under in vivo condition.
Figure 17:
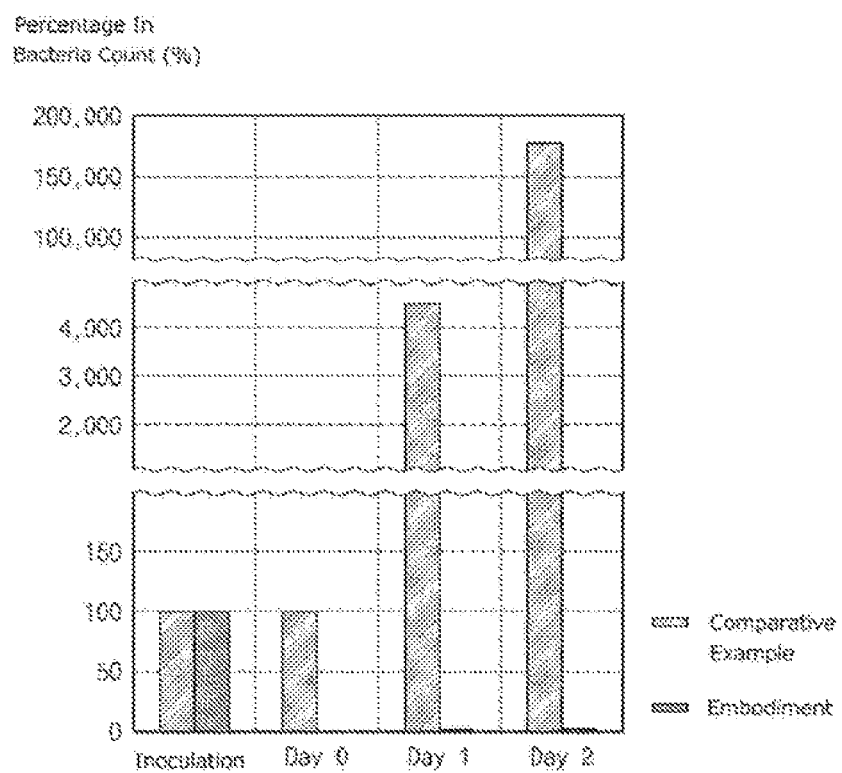
FIG. 17 is a graph illustrating the measurement result of the number of the bacteria based on days under in vivo condition.

FIG. 16 and Table 14 show the variation in the sterilization power depending on days under in vivo condition, and FIG. 17 and Table 15 show the measurement result of the number of bacteria in each day under in vivo condition. In FIG. 17 and Table 15, Comparative example is a non-irradiation group without light irradiation, and Embodiment corresponds to a light irradiation group irradiated with light.

TABLE 14

| Day | Inoculation | 0 | 1 | 2 |
|---|---|---|---|---|
| Sterilization power | 0.00 | 5.00 | 4.09 | 5.29 |
| Error | 0.00 | 0.00 | 0.13 | 0.09 |

TABLE 15

| Day | The number of bacteria (%) | | | | The number of bacteria (log) | | | |
|---|---|---|---|---|---|---|---|---|
| | Inoculation | 0 | 1 | 2 | Inoculation | 0 | 1 | 2 |
| Non-irradiation group | 100 | 100 | 4,466 | 173,780 | 5.00 | 5.00 | 6.65 | 8.24 |
| Light irradiation group | 100 | 0 | 0.36 | 0.89 | 5.00 | 0.00 | 2.56 | 2.95 |

It may be recognized from FIG. 16, FIG. 17, Table 14, and Table 15 that the sterilization power is continuously maintained to 99.99% or more after light is irradiated to the wound at the initial stage, and the number of bacteria is substantially approximate to '0' when the light is irradiated.

Experimental Example 8—Effectiveness Evaluation 2 (In Vivo)

In Embodiment 5, a dose of light for sterilization was recognized under in vivo condition, and the effect of treating the wound by irradiating the light was tested under in vivo condition based on the dose of light for sterilization.

The present test was performed using a mouse. For the mouse, a BALB/c mouse (6-8 weeks old) was used, the back of the mouse was shaved, and then a wound was formed in the diameter of 10 mm in the back of the mouse. After the pathogenic bacteria was inoculated (at 5 log) on the wound, the first light and the second light were sequentially irradiated and repeatedly irradiated six times in total at the same time every day while a dose of the first light (having the wavelength of 405 nm) is 120 J/cm$^2$. However, in the case of the second light, the light of 275 nm was employed with a dose limited to 3 mJ/cm$^2$ based on the allowable level of the human body.

The variation in the shape (especially, an area) of the wound was observed at the same time every day. The size of the wound was observed every day till epithelialization, and the value thereof was recorded.

Figure 18:
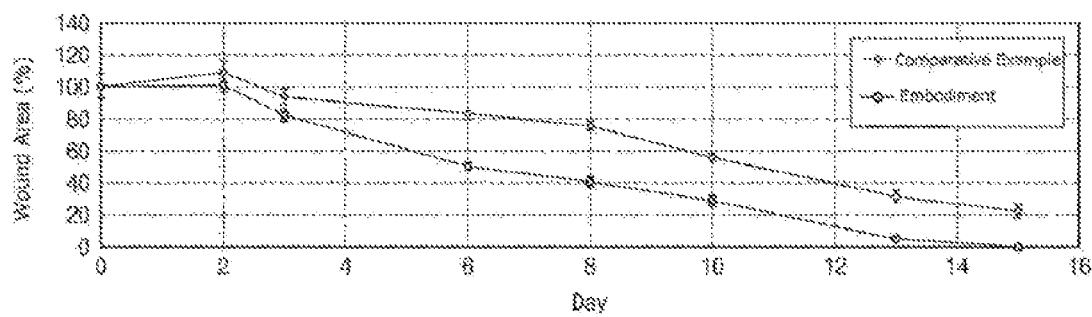
FIG. 18 is a graph illustrating the variation in an area of a wound based on days under in vivo condition.
Figure 19A:
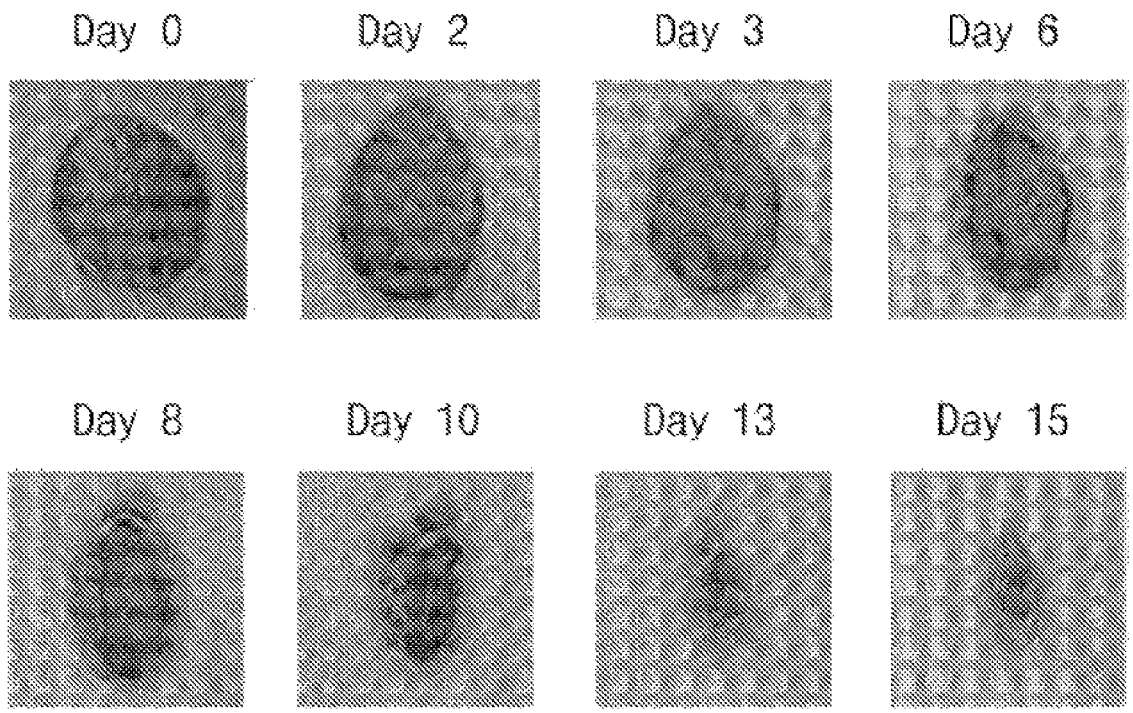
Figure 19B:
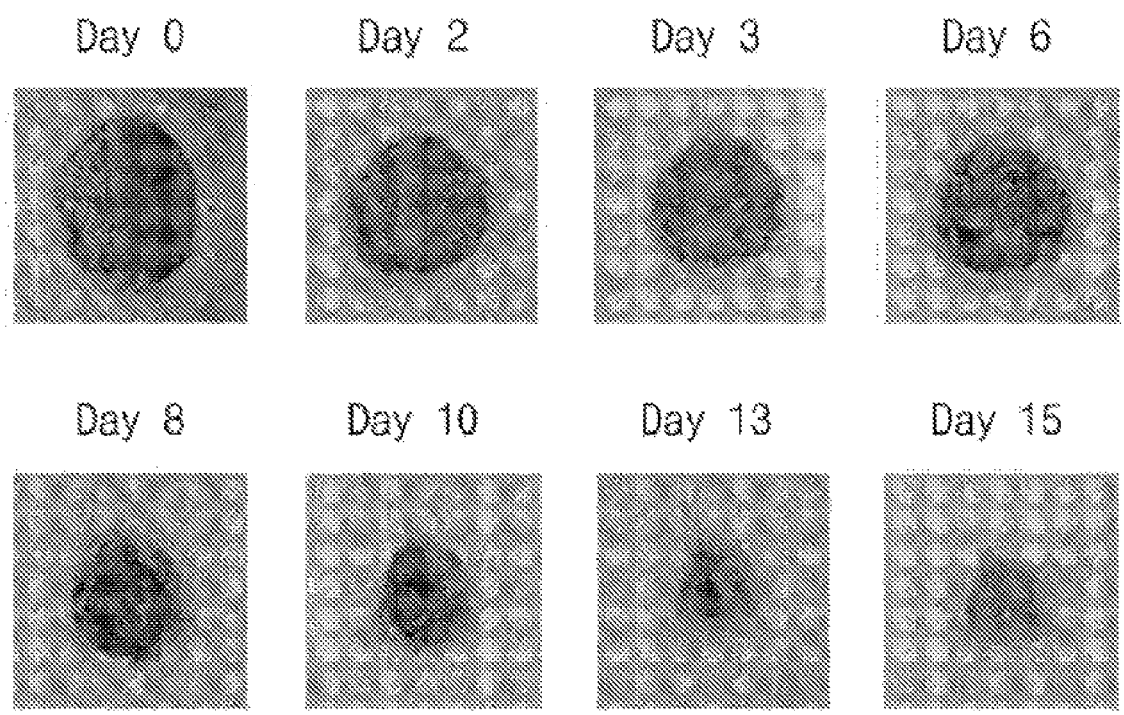

FIG. 18 and Table 16 show the variation in the area of a wound depending on days under in vivo condition. In FIG. 18 and Table 16, Comparative example is a non-irradiation group without light irradiation, and Embodiment corresponds to a light irradiation group irradiated with light. FIGS. 19A and 19B are photographs obtained by capturing images of the shape of the wound area depending on days. FIG. 19A illustrates photographs of a wound in the non-irradiation group, and FIG. 19B illustrates photographs of wounds in the light irradiation group.

TABLE 16

| Day | Inoculation | 0 | 2 | 3 | 6 | 10 | 15 |
|---|---|---|---|---|---|---|---|
| Non-irradiation group | 100.0 | 100.0 | 108.8 | 93.8 | 83.3 | 55.9 | 22.4 |
| Error | 7.8 | 7.8 | 7.0 | 5.0 | 3.8 | 2.7 | 4.2 |

TABLE 16-continued

| Day | Inoculation | 0 | 2 | 3 | 6 | 10 | 15 |
|---|---|---|---|---|---|---|---|
| Light irradiation group | 100.0 | 100.0 | 101.0 | 82.1 | 50.3 | 28.8 | 0.0 |
| Error | 7.8 | 7.8 | 4.1 | 3.6 | 1.9 | 3.2 | 0.0 |

Referring to FIG. 18, Table 16, FIG. 19A, and FIG. 19B, the wound cured was not visibly observed until 2 days from the wound, and the bacteria count in the wound was significantly reduced. Accordingly, it was determined that the sterilization was in progress. A scab was produced from 2 days after the wound and then the area of the wound was gradually reduced. Accordingly, the curing of the wound is in progress from 2 days after the wound. When the scab was produced on the wound, the wound exposed to the outside was disappeared by the scab. Therefore, the additional infection is less caused. However, the size of the scab and the recovery rate of the wound greatly varied depending on the sterilization state until the scab was formed. Although the light irradiation group required 6 days till a time point at which the area of the wound was reduced to 50% in the stage of curing the wound, the non-irradiation group required 10 days till the time point. Further, the epithelialization was achieved on the $15^{th}$ day in the case of the light irradiation group, and not achieved in the case of the non-irradiation group. Accordingly, according to an embodiment of the present disclosure, it may be recognized that the effect of curing the wound is significantly produced when light is irradiated.

Experimental Example 9—Safety Evaluation 1 (In Vivo)

In the above-described experimental example, a DNA mutation state was determined to determine whether the irradiation condition is harmful to the human body.

In the present test, to determine whether the DNA mutation was caused to the tissue which is not infected through light irradiation, the formation degree of a thymine dimer was determined through immunohistochemical analysis. When an excessive amount of UV is irradiated to the DNA, the DNA mutation such as the thymine dimer is caused, so the cell is destroyed. Accordingly, the DNA mutation may be determined based on the formation degree of the thymine dimer.

The present test was performed using a mouse. For the mouse, a BALB/c mouse (6-8 weeks old) was used, the back of the mouse was shaved, and then a wound is formed in the diameter of 10 mm in the back of the mouse by using the punch. After light was irradiated on the wound, the tissue was sampled, the sampled tissue was fixed through formalin and paraffin, and a cut-out fragment was taken. When light was irradiated, the control group was a non-irradiation group in which light was not treated, Experimental group 1 was a light irradiation group in which an excessive amount of UVC was treated, Experimental group 2 was a light irradiation group in which the first light and the second light were sequentially irradiated in the state that a dose of the first light (having the wavelength of 405 nm) is limited to 120 J/cm$^2$ and, a dose of the second light (having the wavelength of 275 nm) is limited to 3 mJ/cm$^2$.

Figure 20A:
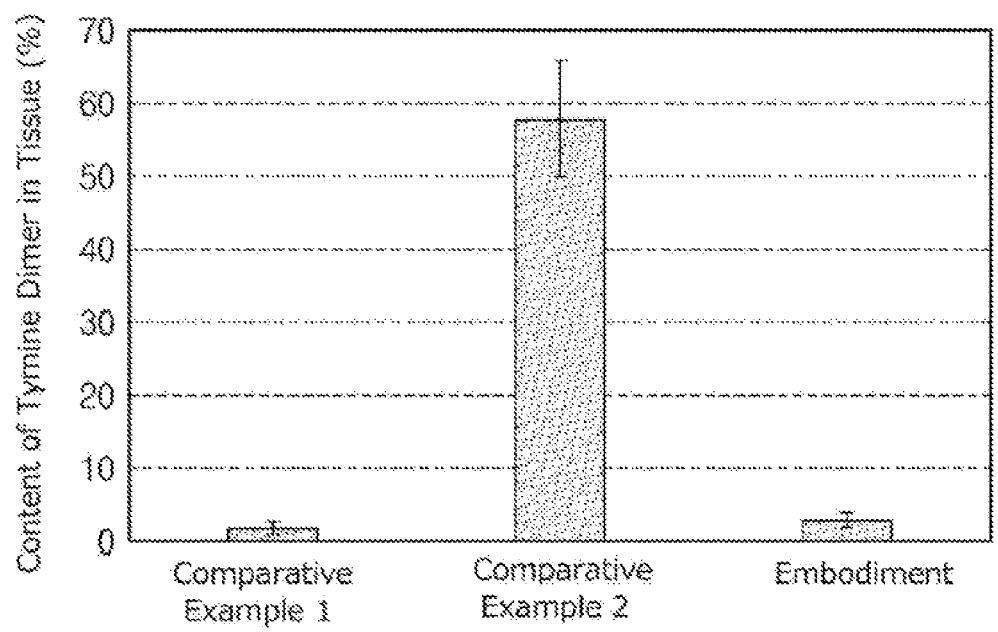
FIG. 20A is a graph illustrating the percentage of a thymine dimer in a tissue.

FIG. 20A and Table 17 illustrate the percentage of a thymine dimer in a tissue. Referring to FIG. 20A and Table 17, although the thymine dimer was found in Experimental group 1, the thymine dimer was not found in Experimental group 2. Accordingly, under the light condition applied according to the embodiments of the present disclosure, it was determined that the DNA mutation was not found even if the light was irradiated to a tissue which was not infected.

TABLE 17

| | Control group | Experimental group 1 | Experimental group 1 |
|---|---|---|---|
| Content (%) | 2 | 58 | 3 |
| Error | 1 | 8 | 1 |

Experimental Example 10—Safety Evaluation 1 (In Vivo)

In the above-described experimental example, the generation state of ROS was determined to determine whether the irradiation condition was harmful to the human body.

The present test is to determine whether the ROS was induced even in the tissue, which was not infected, through light irradiation. When the sterilizing light was irradiated to the infectious bacteria, the ROS was induced to destroy the bacteria.

The present test was performed using a mouse. For the mouse, a BALB/c mouse (6-8 weeks old) was used, the back of the mouse was shaved, and then a wound is formed in the diameter of 10 mm in the back of the mouse by using the punch. After the light was irradiated on the wound, a Dichlorofluorescin diacetate (DCFH-DA) was treated for a part irradiated with light and a light emission was measured with respect to a part stained with DCFH-DA, so it was determined that the ROS was present. DCFH-DA was oxidized by the ROS in the cell to emit fluorescent light. When DCFH-DA was excited, the absorption wavelength was in the range of 445 nm to 490 nm, and the fluorescent wavelength was in the range of 515 nm to 575 nm.

In this case, the control group was a non-treatment group in which non-treatment is added, Experimental group 1 was a group treated with hydrogen peroxide, and Experimental group 2 was a treatment group to which the first light and the second light are sequentially irradiated in the state that a dose of the first light (having the wavelength of 405 nm) is limited to 120 J/cm$^2$, and a dose of the second light (having the wavelength of 275 nm) is limited to 3 mJ/cm$^2$.

Figure 20B:
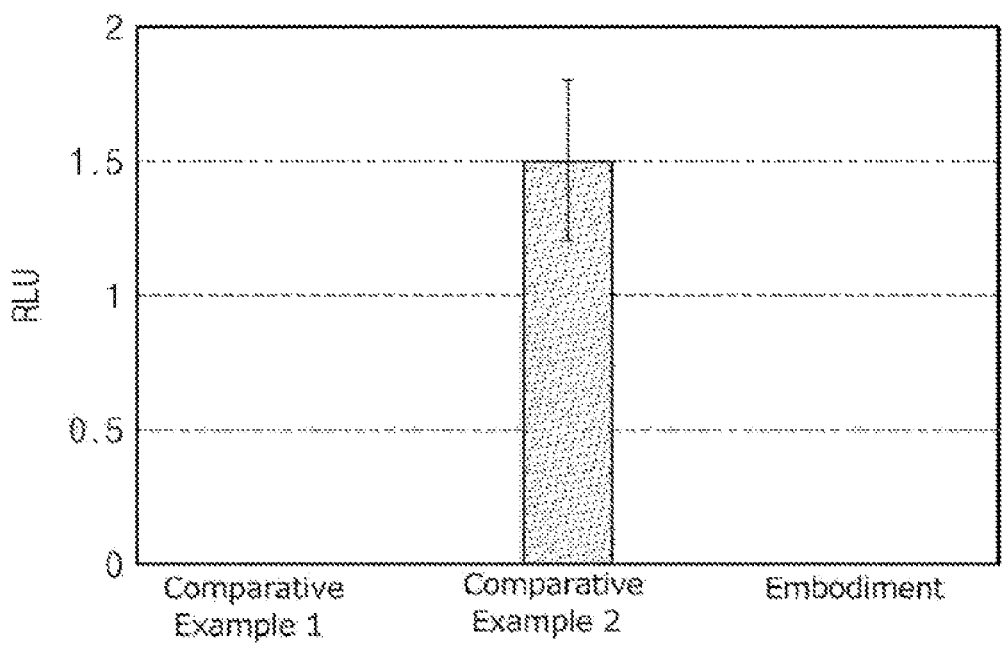
FIG. 20B illustrates a light emission degree of a part stained with DCFH-DA.

FIG. 20B and Table 18 illustrate the light emission degree of a part stained with DCFH-DA. Referring to FIG. 20B and Table 18, fluorescent is emitted in Experimental group 2 and Experimental group 1, so it is determined that ROS is present. However, since fluorescent is not absent in Experiment group 2, so it is determined that ROS is absent. Accordingly, under the light condition applied according to the embodiments of the present disclosure, it was determined that the ROS was not produced even if the light was irradiated to a tissue which was not infected.

TABLE 18

| | Control group | Experimental group 1 | Experimental group 2 |
|---|---|---|---|
| Light emission degree (RLU; relative light units) | 0 | 1.5 | 0 |
| Error | 0 | 0.3 | 0 |

Although an exemplary embodiment of the present disclosure has been described for illustrative purposes, those skilled in the art will appreciate that various modifications, and substitutions are possible, without departing from the scope and spirit of the invention as disclosed in the accompanying claims. Accordingly, the technical scope of the present disclosure is not limited to the detailed description of this specification, but should be defined by the claims.

We claim:

1. A light radiation device comprising:
a housing;
a substrate provided in the housing;
a light source mounted on the substrate,
wherein the light source includes:
a first light source configured to emit a first light having a visible wavelength band;
a second light source configured to emit a second light having an ultraviolet wavelength band;
a window disposed on the light source and covering the substrate and an upper part of the light source, the window configured to transmit light emitted from at least one of the first light source or the second light source;
a fixer disposed on the substrate and configured to fasten the window to the housing; and
a controller configured to allow the first light and the second light to emit sequentially, or at a predetermined interval, regardless of whether an emission of the first light overlaps with an emission of the second light or not, and
wherein the first light source includes a plurality of first light emitters and the second light source includes a plurality of second light emitters,
wherein a number of the plurality of first light emitters is different from a number of the plurality of second light emitters,
wherein each of the first light source and the second light source includes an optic to control the light emitted from at least one of the first light source or the second light source,
wherein the controller is further configured to allow to (1) apply the first light without interruption, (2) apply the second light discontinuously, and (3) allow an application of the first light to start before an application of the second light.

2. The light radiation device of claim 1, wherein the controller is configured to control whether the light is emitted from at least one of the first light source or the second light source, an amount of the light, an intensity of the light, a timing or a duration of at least one of the emission of the first light or the emission of the second light.

3. The light radiation device of claim 2, wherein the controller is configured to allow the first light to be irradiated for a first duration, and the second light to be irradiated for a second duration shorter than the first duration.

4. The light radiation device of claim 3, wherein the controller is configured to allow the second light to start to be irradiated before the first light stops irradiating, and at least portions of the first duration and the second duration are overlapping to each other.

5. The light radiation device of claim 4, wherein the controller is configured to allow the first light to be continuously irradiated during the first duration.

6. The light radiation device of claim 4, wherein the controller is configured to allow the second light to be discontinuously irradiated during the second duration.

7. The light radiation device of claim 1, wherein the optic includes a lens to disperse the light.

8. The light radiation device of claim 1, wherein the optic includes a lens to focus the light.

9. A light radiation device, comprising:
a housing;
a substrate disposed in the housing;
a first light source disposed on the substrate and configured to emit a first light in a visible wavelength band;
a second light source disposed on the substrate and configured to emit a second light in an ultraviolet wavelength band;
a window disposed on the housing and covering the substrate and upper parts of the first light source and the second light source, the window configured to transmit light emitted from at least one of the first light source or the second light source;
a fixer disposed on the housing and configured to be coupled to the window; and
a controller configured to control whether the light is emitted from at least one of the first light source or the second light source, an amount of the light, an intensity of the light, a timing or a duration of at least one of an emission of the first light or an emission of the second light,
wherein each of the first light source and the second light source includes an optic to control the light emitted from at least one of the first light source or the second light source,
wherein the controller is further configured to allow to (1) apply the first light without interruption, (2) apply the second light discontinuously, and (3) allow an application of the first light to start before an application of the second light.

10. The light radiation device of claim 9, wherein the controller is configured to allow the first light to be irradiated for a first duration, and the second light to be irradiated for a second duration shorter than the first duration.

11. The light radiation device of claim 10, wherein the controller is configured to allow the second light to start to be irradiated before the first light stops irradiating, and at least portions of the first duration and the second duration are overlapping to each other.

12. The light radiation device of claim 11, wherein the controller is configured to allow the first light to be continuously irradiated during the first duration.

13. The light radiation device of claim 11, wherein the controller is configured to allow the second light to be discontinuously irradiated during the second duration.

14. The light radiation device of claim 9, wherein the optic includes a lens to disperse the light.

15. The light radiation device of claim 9, wherein the optic includes a lens to focus the light.

16. A light radiation device, comprising:
a housing;
a substrate disposed in the housing;
a first light source disposed on the substrate and configured to emit a first light corresponding to a visible light;

a second light source disposed on the substrate and configured to emit second light having a peak wavelength in an ultraviolet wavelength range;

a window disposed on the housing and covering the substrate and upper parts of the first light source and the second light source, the window configured to transmit light emitted from at least one of the first light source or the second light source;

a fixer disposed on the housing and configured to be coupled to the window; and a controller configured to allow the first light and the second light to be emitted sequentially, or at a predetermined interval, regardless of whether an emission of the first light overlaps with an emission of the second light or not, and wherein each of the first light source and the second light source includes an optic to control the light emitted from at least one of the first light source or the second light source, wherein the controller is further configured to allow to (1) apply the first light without interruption, (2) apply the second light discontinuously, and (3) allow an application of the first light to start before an application of the second light.

17. The light radiation device of claim 16, wherein the controller is configured to allow the first light to be irradiated for a first duration, and the second light to be irradiated for a second duration shorter than the first duration.

18. The light radiation device of claim 17, wherein the controller is configured to allow the second light to start to be irradiated before the first light stops irradiating, and at least portions of the first duration and the second duration are overlapping to each other.

19. The light radiation device of claim 18, wherein the controller is configured to allow the first light to be continuously irradiated during the first duration.

20. The light radiation device of claim 18, wherein the controller is configured to allow the second light to be discontinuously irradiated during the second duration.

* * * * *